United States Patent [19]
Griesbach, III et al.

[11] Patent Number: 5,643,653
[45] Date of Patent: Jul. 1, 1997

[54] SHAPED NONWOVEN FABRIC

[75] Inventors: Henry Louis Griesbach, III, Atlanta; Richard Daniel Pike, Norcross; Sharon Watkins Gwaltney, Woodstock; Ruth Lisa Levy, Sugar Hill; Lawrence Howell Sawyer, Roswell; Richard Macferran Shane, Duluth; Philip Anthony Sasse, Alpharetta, all of Ga.

[73] Assignee: Kimberly-Clark Corporation, Neenah, Wis.

[21] Appl. No.: 447,340

[22] Filed: May 22, 1995

Related U.S. Application Data

[62] Division of Ser. No. 435,239, May 5, 1995, which is a continuation of Ser. No. 55,449, Apr. 29, 1993, abandoned.

[51] Int. Cl.$^6$ .............................. B32B 1/10; B32B 3/30; D04H 3/16
[52] U.S. Cl. .................... 428/120; 428/131; 428/137; 428/156; 428/172; 604/358; 604/366; 604/370; 604/372; 442/350
[58] Field of Search .................... 428/131, 137, 428/156, 172, 120, 288, 296; 604/358, 366, 370, 372

[56] References Cited

U.S. PATENT DOCUMENTS

| Re. 31,599 | 6/1984 | Rasen et al. ............... 156/167 |
| 2,671,496 | 3/1954 | Chavannes et al. .. |
| 2,940,133 | 6/1960 | Heritage ............... 19/156 |
| 2,986,780 | 6/1961 | Bletzinger ............... 19/156 |
| 3,330,009 | 7/1967 | Hynek ............... 19/161 |
| 3,338,992 | 8/1967 | Kinney ............... 264/24 |
| 3,341,394 | 9/1967 | Kinney . |
| 3,423,266 | 1/1969 | Davies et al. ............... 156/167 |
| 3,502,538 | 3/1970 | Petersen . |
| 3,502,763 | 3/1970 | Hartmann ............... 264/210 |
| 3,542,615 | 11/1970 | Dobo et al. ............... 156/181 |
| 3,595,245 | 7/1971 | Buntin et al. ............... 131/269 |
| 3,595,731 | 7/1971 | Davies et al. . |
| 3,676,242 | 7/1972 | Prentice ............... 156/62.4 |
| 3,686,049 | 8/1972 | Manner et al. ............... 156/167 |
| 3,692,618 | 9/1972 | Dorschner et al. ............... 161/72 |

(List continued on next page.)

FOREIGN PATENT DOCUMENTS

| 803714 | 1/1969 | Canada . |
| 0138549 | 4/1985 | European Pat. Off. ......... D04H 1/56 |
| 0168225 | 1/1986 | European Pat. Off. ......... D04H 1/54 |
| 0565392 | 10/1993 | European Pat. Off. ......... D04H 1/54 |
| 1089414 | 11/1964 | United Kingdom . |
| 1217892 | 12/1970 | United Kingdom . |
| WO8805838 | 8/1988 | WIPO ............... D04H 1/00 |
| 92/16364 | 10/1992 | WIPO ............... B32B 5/02 |
| WO9315251 | 8/1993 | WIPO ............... D04H 3/16 |

OTHER PUBLICATIONS

*INDA Journal of Nonwovens Research*, Spring 1991, vol. 3, No. 2, p. 27.
Naval Research Laboratory Report 111437, Apr. 15, 1954.
"Superfine Thermoplastic Fibers" by Wendt in Industrial and Engineering Chemistry, vol. 48, No. 8, 1956, pp. 1342–1346.
"Apertured Nonwoven Fabric Process"—*The New Nonwovens World* Summer 1992, pp. 56–57.

*Primary Examiner*—James C. Cannon
*Attorney, Agent, or Firm*—William D. Herrick

[57] ABSTRACT

A shaped nonwoven fabric comprises continuous spunbond filaments made by directly forming the spunbond filaments into a web in a single process. The fabric has an array of discrete surface features such as apertures or projections, or both. The spunbond filaments are bonded together with an adhesive polymeric component so that the shape of the fabric is retained. The fabric can be engineered to have particular fluid handling properties, strength properties, abrasive properties and aesthetic properties. Articles such as personal care products, garments, medical products and cleaning products are also disclosed.

24 Claims, 11 Drawing Sheets

U.S. PATENT DOCUMENTS

| | | | |
|---|---|---|---|
| 3,704,198 | 11/1972 | Prentice | 161/148 |
| 3,715,251 | 2/1973 | Prentice | 156/62.8 |
| 3,750,236 | 8/1973 | Kalwaites | 19/161 P |
| 3,769,659 | 11/1973 | Kalwaites | 19/161 P |
| 3,802,817 | 4/1974 | Matsuki et al. | 425/66 |
| 3,837,988 | 9/1974 | Hennen et al. | 161/67 |
| 3,909,009 | 9/1975 | Cvetko et al. | 274/37 |
| 4,041,203 | 8/1977 | Brock et al. | 428/157 |
| 4,042,740 | 8/1977 | Krueger | 428/138 |
| 4,100,324 | 7/1978 | Anderson et al. | 428/288 |
| 4,103,058 | 7/1978 | Humlicek | 428/171 |
| 4,118,531 | 10/1978 | Hauser | 428/224 |
| 4,189,338 | 2/1980 | Ejima et al. | 156/167 |
| 4,280,860 | 7/1981 | Shen et al. | 156/167 |
| 4,340,563 | 7/1982 | Appel et al. | 264/518 |
| 4,425,126 | 1/1984 | Butterworth et al. | 604/366 |
| 4,488,928 | 12/1984 | Ali Khan et al. | 156/495 |
| 4,555,811 | 12/1985 | Shimalla | 2/51 |
| 4,588,630 | 5/1986 | Shimalla | 428/131 |
| 4,592,943 | 6/1986 | Cancian et al. | 428/171 |
| 4,595,629 | 6/1986 | Mays | 428/286 |
| 4,681,801 | 7/1987 | Eian et al. | 428/283 |
| 4,684,570 | 8/1987 | Malaney | 428/296 |
| 4,741,941 | 5/1988 | Englebert et al. | 428/71 |
| 4,756,786 | 7/1988 | Malaney | 156/308.2 |
| 4,784,892 | 11/1988 | Storey et al. | 428/172 |
| 4,883,707 | 11/1989 | Newkirk | 428/219 |
| 4,997,611 | 3/1991 | Hartmann | 264/210.8 |
| 5,057,361 | 10/1991 | Sayovitz et al. | 428/290 |
| 5,098,764 | 3/1992 | Drelich et al. | 428/131 |
| 5,143,779 | 9/1992 | Newkirk et al. | 428/218 |
| 5,180,620 | 1/1993 | Mende | 428/138 |
| 5,242,632 | 9/1993 | Mende | 264/6 |

SHAPED NONWOVEN FABRIC

This application is a divisional of a file wrapper continuation filed May 5, 1995, Ser. No. 08/435,239 of application Ser. No. 08/055,449 entitled "Shaped Nonwoven Fabric and Method for Making the Same" and filed in the U.S. Patent and Trademark Office on Apr. 29, 1993 now abandoned.

TECHNICAL FIELD

This invention relates to shaped or 3-dimensional nonwoven fabrics which include an array of surface features such as projections, apertures, or both.

BACKGROUND OF THE INVENTION

Nonwoven fabrics are useful for a wide variety of applications, including absorbent personal care products, garments, medical applications, and cleaning applications. Nonwoven personal care products include infant care items such as diapers, child care items such as training pants, feminine care items such as sanitary napkins, and adult care items such as incontinence products. Nonwoven garments include protective workwear and medical apparel such as surgical gowns. Other nonwoven medical applications include nonwoven wound dressings and surgical dressings. Cleaning applications for nonwovens include towels and wipes. Still other uses of nonwoven fabrics are well known. The foregoing list is not considered exhaustive.

Various properties of nonwoven fabrics determine the suitability of nonwoven fabrics for different applications. Nonwoven fabrics may be engineered to have different combinations of properties to suit different needs. Variable properties of nonwoven fabrics include liquid-handling properties such as wettability, distribution, and absorbency, strength properties such as tensile strength and tear strength, softness properties, durability properties such as abrasion resistance, and aesthetic properties. The physical shape of a nonwoven fabric also affects the functionality and aesthetic properties of the nonwoven fabric. Nonwoven fabrics are initially made into sheets which, when laid on a flat surface, may have a substantially planar, featureless surface or may have an array of surface features such as aperture or projections, or both. Nonwoven fabrics with apertures or projections are often referred to as three-dimensional or shaped nonwoven fabrics. The present invention relates to three-dimensional or shaped nonwoven fabrics.

The manufacture of nonwoven fabrics is a highly-developed art. Generally, nonwoven webs and their manufacture involve forming filaments or fibers and depositing the filaments or fibers on a carrier in such a manner so as to cause the filaments or fibers to overlap or entangle. Depending on the degree of web integrity desired, the filaments or fibers of the web may then be bonded by means such as an adhesive, the application of heat or pressure, or both, sonic bonding techniques, or hydroentangling, or the like. There are several methods of producing fibers or filaments within this general description; however, two commonly used processes are known as spunbonding and meltblowing and the resulting nonwoven fabrics are known as spunbond and meltblown fabrics, respectively. As used herein, polymeric fibers and filaments are referred to generically as polymeric strands. Filaments means continuous strands of material and fibers mean cut or discontinuous strands having a definite length.

Generally described, the process for making spunbond nonwoven fabrics includes extruding thermoplastic material through a spinneret and drawing the extruded material into filaments with a stream of high-velocity air to form a random web on a collecting surface. Such a method is referred to as meltspinning. Spunbond processes are generally defined in numerous patents including, for example, U.S. Pat. No. 4,692,618 to Dorschner, et al.; U.S. Pat. No. 4,340,563 to Appel, et al.; U.S. Pat. No. 3,338,992 to Kinney; U.S. Pat. No. 3,341,394 to Kinney; U.S. Pat. No. 3,502,538 to Levy; U.S. Pat. No. 3,502,763 to Hartmann; U.S. Pat. No. 3,909,009 to Hartmann; U.S. Pat. No. 3,542,615 to Dobo, et al., and Canadian Patent 803,714 to Harmon.

On the other hand, meltblown nonwoven fabrics are made by extruding a thermoplastic material through one or more dies, blowing a high-velocity stream of air past the extrusion dies to generate an air-conveyed meltblown fiber curtain and depositing the curtain of fibers onto a collecting surface to form a random nonwoven web. Meltblowing processes are generally described in numerous publications including, for example, an article titled "Superfine Thermoplastic Fibers" by Wendt in *Industrial and Engineering Chemistry*, Vol. 48, No. 8, (1956), at pp. 1342–1346, which describes work done at the Naval Research Laboratories in Washington, D.C.; Naval Research Laboratory Report 111437, dated Apr. 15, 1954; U.S. Pat. Nos. 4,041,203; 3,715,251; 3,704,198; 3,676,242; and U.S. Pat. No. 3,595,245; and British Specification 1,217,892.

Spunbond and meltblown nonwoven fabrics can usually be distinguished by the diameters and the molecular orientation of the filaments or fibers which form the fabrics. The diameter of spunbond and meltblown filaments or fibers is the average cross-sectional dimension. Spunbond filaments or fibers typically have average diameters greater than 6 microns and often have average diameters in the range of 15 to 40 microns. Meltblown fibers typically have average diameters of less than 6 microns. However, because larger meltblown fibers, having diameters of at least 6 microns may also be produced, molecular orientation can be used to distinguish spunbond and meltblown filaments and fibers of similar diameters. For a given fiber or filament size and polymer, the molecular orientation of a spunbond fiber or filament is typically greater than the molecular orientation of a meltblown fiber. Relative molecular orientation of polymeric fibers or filaments can be determined by measuring the tensile strength and birefringence of fibers or filaments having the same diameter.

Tensile strength of fibers and filaments is a measure of the stress required to stretch the fiber or filament until the fiber or filament breaks. Birefringence numbers are calculated according to the method described in the spring 1991 issue of *INDA Journal of Nonwovens Research*, (Vol. 3, No. 2, p. 27). The tensile strength and birefringence numbers of polymeric fibers and filaments vary depending on the particular polymer and other factors; however, for a given fiber or filament size and polymer, the tensile strength of a spunbond fiber or filament is typically greater than the tensile strength of a meltblown fiber and the birefringence number of a spunbond fiber or filament is typically greater than the birefringence number of a meltblown fiber.

A number of patents disclose methods for making shaped or three-dimensional nonwoven fabrics. For example, U.S. Pat. No. 5,098,764 to Drelich, et al., discloses a nonwoven yarn-like fabric with a net-like structure having apertures. The fabric is formed by laying a web of staple fibers on a surface having an array of holes and projections and spraying the web with high-pressure water to form apertures in the web and entangle the fibers. U.S. Pat. No. 4,741,941 to Engelbert, et al., discloses nonwoven webs having apertures in the fabric or projections extending from the fabric, or both. In this patent, the nonwoven webs are made by forming meltblown or spunbond webs onto a surface which has apertures or projections, or both. In addition, U.S. Pat. No. 4,488,928 to Alikhan, et al., discloses a nonwoven web with puffed regions formed by passing a preformed web between two open mesh screens and thermally bonding the web.

Despite the prior advances in the art as described above, there is still a need for improved nonwoven fabrics having surface features such as apertures or projections or both and methods for forming such materials.

SUMMARY OF THE INVENTION

Accordingly, an object of the present invention is to provide an improved shaped nonwoven fabric and process for making the same.

Another object of the present invention is to to provide an improved shaped nonwoven fabric made with spunbond filaments and a process for making the same.

Another object of the present invention is to provide an improved nonwoven fabric having apertures or projections, or both, and a process for making the same.

Still another object of the present invention is to provide a nonwoven fabric with improved fluid-handling properties.

Yet another object of the present invention is to provide improved shaped nonwoven articles such as personal care articles, garments, medical articles, and cleaning articles, and the like.

Thus, the present invention provides a shaped nonwoven fabric, a process for making the nonwoven fabric, and articles made with such fabric. The nonwoven fabric of the present invention is made by directly forming spunbond filaments into a web in a single process and has an array of discrete surface features such as apertures or projections, or both. The spunbond filaments are bonded together with an adhesive polymeric component so that the shape of the fabric is retained. The fabric of the present invention can be engineered to have particular fluid handling properties. The surface features of the fabric can be designed to direct flow 3-dimensionally through the fabric. The features of the fabric can also be designed to enhance the strength, resilience, abrasive properties, and the aesthetic properties of the fabric. The fabric of the present invention also can be designed to perform as a separation layer in various applications for improved skin dryness of the wearer. Other advantages of the fabric of the present invention are explained below.

More particularly, the nonwoven fabric of the present invention includes meltspun and drawn continuous spunbond polymeric filaments which extend substantially continuously along the length of the fabric. The filaments have an average effective diameter from about 6 to about 40 microns and form an array of discrete surface features in the fabric. Each filament has a primary polymeric component extending continuously along the length of the filament. The filaments are bonded together without the use of compression and with an adhesive polymeric component which adheres the respective primary components of the filaments together, so that fabric is substantially uncompressed.

As mentioned above, the features in the fabric of the present invention may include apertures or projections, or both. Preferably, the surface features of the fabric of the present invention have a minimum size which is measured in a plane extending between adjacent land areas. In other words, each of the surface features has a cross-sectional area which extends between adjacent land areas, and preferably, the cross-sectional area of at least some of the individual surface features of the fabric has a minimum dimension of at least 0.03 inches. For example, if the cross-sectional area of the feature is rectangular, the minimum dimension is the length of the shortest side of the rectangle.

When the surface features of the fabric include projections extending from the fabric, the projections are substantially uncompressed because the filaments are bonded together with an adhesive polymeric component and are not bonded with compression. Depending on the particular method of formation of the fabric, the basis weight across the fabric can vary. In an embodiment wherein the basis weight varies, the projections are substantially filled with continuous filaments. In that embodiment, the projections are preferably separated by land areas and have a basis weight greater than the basis weight of adjacent land areas.

In a more particular embodiment wherein the projections have a basis weight greater than the basis weight of the land areas, the land areas of the fabric have portions of higher density than other lower density portions and the higher density portions include aligned filaments connecting adjacent projections. In this more particular embodiment, the fabric has zones of different fluid handling properties. The lower density open zones of the land areas are suitable for fluid intake, the higher density zones of the land areas are suitable for wicking fluid, and the projections extending from the fabric are useful for liquid collection and transfer through the fabric and separation of the fabric from an adjacent surface. This particular embodiment is useful as a liner or liner/surge layer in a personal care article.

In an embodiment of the present invention having projections, the basis weight of the projections is preferably at least 30% greater than the basis weight of adjacent land areas. More particularly, in such an embodiment, the length and width of the fabric defines a reference surface area and the projections each have a cross-sectional area which forms part of the reference surface area and extends between adjacent land areas. Preferably, the cross-sectional areas of the projections total from about 10 to about 95% of the reference surface area. More preferably, the cross-sectional areas of the projections total from about 25 to about 50% of the reference surface area. Still more preferably, the projections have a height of at least about 0.05 inches.

The spunbond filaments in the fabric of the present invention preferably have a natural helical crimp to add loft and resilience to the fabric. Preferably, these continuous filaments have at least about 3.0 natural helical crimps per extended inch when measured according to ASTM D 3937-90. In a particularly preferred embodiment, the continuous spunbond polymeric filaments are multicomponent filaments. The multicomponent filaments comprise the primary polymeric component of the filaments and the adhesive component. The primary and adhesive components are arranged in substantially distinct zones across the cross-section of the multicomponent filaments and extend continuously along the length of the multicomponent filaments. The adhesive component constitutes at least a portion of the peripheral surface of the multicomponent filaments continuously along the length of the multicomponent filaments. When the polymeric components are properly selected and arranged, the multicomponent filaments develop natural helical crimp.

The continuous filaments in the fabric of the present invention preferably have an average effective diameter from about 6 to about 40 microns. Such continuous polymeric filaments in the fabric of the present invention are not meltblown fibers, although the nonwoven web of the present invention can include meltblown polymeric fibers as the adhesive component or as a means for entangling the spunbond filaments.

Generally described, the process of the present invention includes directly forming spunbond polymeric filaments onto a shaped forming surface, so that the nonwoven fabric has a shape which corresponds to the shape of the forming surface, and bonding together the filaments of the web with an adhesive to integrate the web without the application of bonding pressure. With the process of the present invention, the shaped spunbond nonwoven fabric retains a shape which corresponds to that of the forming surface.

More particularly, the process of the present invention includes the steps of:

a) meltspinning continuous spunbond polymeric filaments;

b) drawing the continuous filaments;

c) quenching the filaments;

d. thereafter, collecting the drawn filaments on a moving forming surface to form a nonwoven fabric web of continuous filaments, the forming surface being a least partially foraminous and having an array of discret surface features;

e. concurrently with collecting the drawn filaments on the forming surface, forcing air through the filaments and the forming surface to arrange the filaments into a web which has an array of surface features corresponding to the array of surface features of the forming surface;

f. bonding together the filaments of the web with an adhesive to integrate the web without the application of pressure: and g. separating the integrated web from the forming surface.

The spunbond filaments must be quenched sufficiently before being collected on the foaming surface so that the filaments can be arranged by the forced air passing through the filaments and forming surface. Quenching the filaments reduces the tackiness of the filaments so that the filaments do not adhere to one another too tightly before being bonded and can be moved or arranged on the forming surface.

According to one embodiment, the spunbond filaments are bonded after the web is separated from the forming surface. In such an embodiment, the spunbond filaments must be formed into a web which has sufficient integrity without adhesive bonding to be separated from the forming surface and then bonded without the surface features of the fabric disintegrating. One method of accomplishing this is by combining meltblown polymeric fibers with the spunbond filaments to form the web whereby the spunbond filaments and meltblown fibers are entangled sufficiently so that the array of surface features of the web remain intact during the separating and bonding steps.

According to another embodiment, the spunbond filaments are bonded before the separation step so that the filaments are bonded while still on the forming surface. One suitable method includes combining meltblown adhesive fibers with the spunbond continuous filaments before collection of the spunbond filaments on the forming surface and bonding the filaments by heating the resulting web to activate the adhesive fibers. Another suitable method includes combining a heat-activated adhesive polymeric powder with the filaments and bonding the filaments by heating the web to activate the adhesive powder. Still another suitable method includes combining discrete strands of heat-activated adhesive component with the continuous spunbond filaments before colection of the spunbond filaments on the forming surface and bonding the filaments by heating the web to activate the adhesive strands. The web is preferably heated by forcing heated air through the web and the forming surface.

A preferred method of bonding the web includes, that wherein the continuous polymeric filaments are multicomponent filaments which are described above. Such a method includes heating the web to a temperature which is sufficient to activate the adhesive component and is less than the melting temperature of the primary polymeric component of the filaments. Preferably, the primary polymeric component and the adhesive component are selected so that the continuous multicomponent filaments are capable of developing a latent natural helical crimp. Prior to the step of collecting the filaments on the forming surface, the multicomponent filaments are at least partially quenched so that the filaments have latent helical crimp and then the latent helical crimp is activated. The filaments are crimped before the step of collecting the filaments on the forming surface. However, it should be understood that it is not necessary that the filaments be multicomponent filaments to be crimped.

Still more particularly, the surface features of the forming surface each have a cross-section extending between adjacent land areas and the cross-sections of at least some of the individual surface features of the forming surface have a minimum dimension of at least 0.03 inches. Such an arrangement forms surface features in the fabric having the corresponding minimum dimension.

When it is desirable to make a fabric with projections, the forming surface includes recesses so that the projections of the fabric correspond to the shape of the recesses. When it is desirable to make a fabric wherein the basis weight varies across the fabric, the surface features of the forming surface include air permeable recesses separated by less air permeable land areas so that during the step of forcing air through the filaments and the forming surface, the pressure drop across the land areas is greater than the pressure drop across the recesses and the filaments are drawn into the recesses in the forming surface. Preferably, the forming surface has a length and a width which define a reference surface area and the recesses each have an open cross-sectional area which forms part of the reference surface area and extends between adjacent less-porous land areas. The open cross-sectional areas of the recesses preferably total from about 10 to about 95% of the referenced surface area and more preferably from about 25 to about 50% of the reference surface area. Also preferably, the recesses have a depth of at least about 0.05 inches. Still further, the cross-sectional area of the recesses preferably have a minimum dimension of at least 0.05 inches. The resulting nonwoven fabric has projections with cross-sectional sectional areas which assume the dimensions of the cross-sectional areas of the recesses in the forming surface.

When it is desired to make an apertured nonwoven fabric, the surface features of the forming surface include non-porous projections separated by foraminous areas. The projections have a cross-section shaped so that, during the concurrent steps of collecting the filaments on the forming surface and forcing air through the filaments and forming surface, the filaments are drawn along the projections towards the foraminous land areas of the forming surface, so that the surface features of the fabric include apertures which correspond to the shape of the cross-sections of the projections. The cross-sectional area of the projections preferably have a minimum dimension of at least 0.03 inches.

The nonwoven fabric of the present invention can be used to make a variety of articles including personal care absorbent articles such as infant diapers, adult incontinence products, feminine care absorbent products, and training pants. The fabric of the present invention may also be used to make garments, medical products such as wound dressings, and cleaning products such as towels and wipes.

Still further objects and the broad scope of the applicability of the present invention will become apparent to those of skill in the art from the details given hereafter. However, it should be understood that the detailed description of the preferred embodiments of the present invention is given only by way of illustration because various changes and modifications well within the spirit and scope of the invention should become apparent to those of skill in the art in view of the following detailed description.

DETAILED DESCRIPTION OF THE INVENTION

As discussed above, the present invention provides a shaped nonwoven fabric directly formed on a shaped forming surface with continuous spunbond filaments in a single forming process. The fabric of the present invention assumes a shape which corresponds to the shape of the forming surface and thus has features such as projections or apertures, or both. The present invention also comprehends a relatively efficient and economical process for making such fabric and articles made with such fabric. The fabric of the present invention is particularly useful for making personal care articles, garments, medical products, and cleaning products.

A preferred embodiment of the fabric of the present invention includes continuous multicomponent polymeric filaments comprising a primary polymeric component and an adhesive polymeric component. More particularly, this embodiment includes continuous bicomponent filaments comprising a primary polymeric component A and an adhesive polymeric component B. The bicomponent filaments have a cross-section, a length, and a peripheral surface. The components A and B are arranged in substantially distinct zones across the cross-section of the bicomponent filaments and extend continuously along the length of the bicomponent filaments. The adhesive component B constitutes at least a portion of the peripheral surface of the bicomponent filaments continuously along the length of the bicomponent filaments. The bicomponent spunbond filaments have an average diameter from about 6 to about 40 microns, and preferably from about 15 to about 40 microns.

Figure 2A:
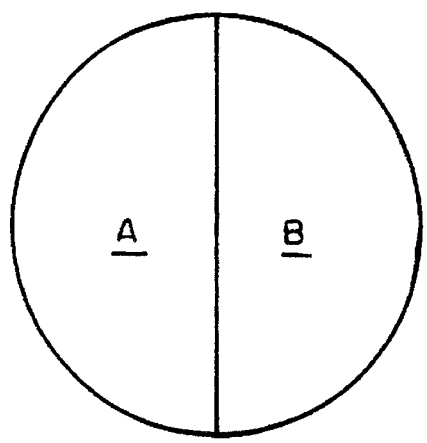
FIG. 2A is a schematic drawing illustrating the cross-section of a filament made according to a embodiment of the present invention with the primary component A and the adhesive component B in a side-by-side arrangement.
Figure 2B:
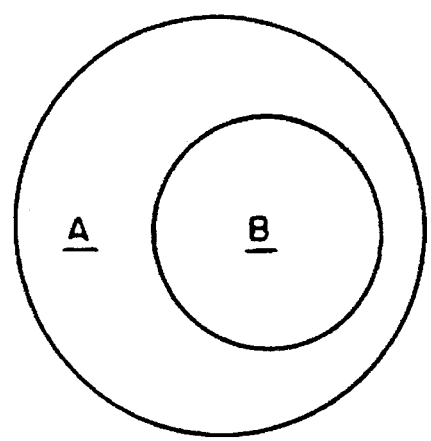
FIG. 2B is a schematic drawing illustrating the cross-section of a multicomponent filament made according to a embodiment of the present invention with the primary component A and the adhesive component B in an eccentric sheath/core arrangement.
Figure 2C:
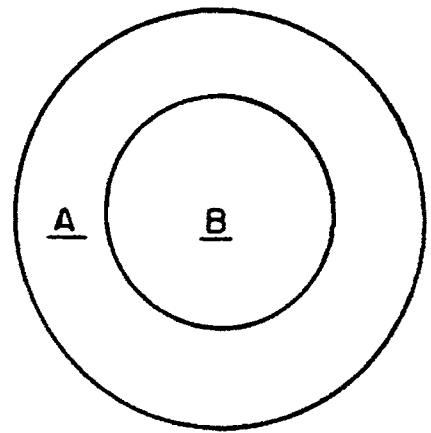
FIG. 2C is a schematic drawing illustrating the cross-section of a multicomponent filament made according to a embodiment of the present invention with the primary component A and the adhesive component B in a concentric sheath/core arrangement.

The components A and B are arranged in either a side-by-side arrangement as shown in FIG. 2A or an eccentric sheath/core arrangement as shown in FIG. 2B to obtain filaments which exhibit a natural helical crimp. Alternatively, the components A and B can be arranged in a concentric sheath core arrangement as shown in FIG. 2C if little or no crimp is desired. Primary polymeric component A is the core of the filament and adhesive polymeric component B is the sheath in the sheath/core arrangement. Methods for extruding multicomponent polymeric filaments into such arrangements are well-known to those of ordinary skill in the art.

A wide variety of polymers are suitable to practice the present invention including polyolefins (such as polyethylene, polypropylene and polybutylene), polyesters, polyamides, polyurethanes, and the like. Primary component A and adhesive component B can be selected so that the resulting bicomponent filament is capable of developing a natural helical crimp. Preferably, primary polymer component A has a melting temperature which is greater than the melting temperature of adhesive polymer component B.

Preferably, primary polymer component A comprises polypropylene or random copolymer of propylene and ethylene. Adhesive polymer component B preferably comprises polyethylene or random copolymer of propylene and ethylene. Preferred polyethylenes include linear low density polyethylene and high density polyethylene. In addition, adhesive polymer component B may comprise additives for enhancing the natural helical crimp of the filaments, lowering the bonding temperature of the filaments, and enhancing the abrasion resistance, strength and softness of the resulting fabric.

Suitable materials for preparing the multicomponent filaments of the fabric of the present invention include PD-3445 polypropylene available from Exxon of Houston, Tex., random copolymer of propylene and ethylene available from Exxon, ASPUN 6811A and 2553 linear low density polyethylene available from Dow Chemical Company of Midland, Mich., and 25355 and 12350 high density polyethylene available from Dow Chemical Company.

When polypropylene is component A and polyethylene is component B, the bicomponent filaments may comprise from about 20 to about 80% by weight polypropylene and from about 80 to about 20% polyethylene. More preferably, the filaments comprise from about 40 to about 60% by weight polypropylene and from about 60 to about 40% by weight polyethylene.

Figure 1A:
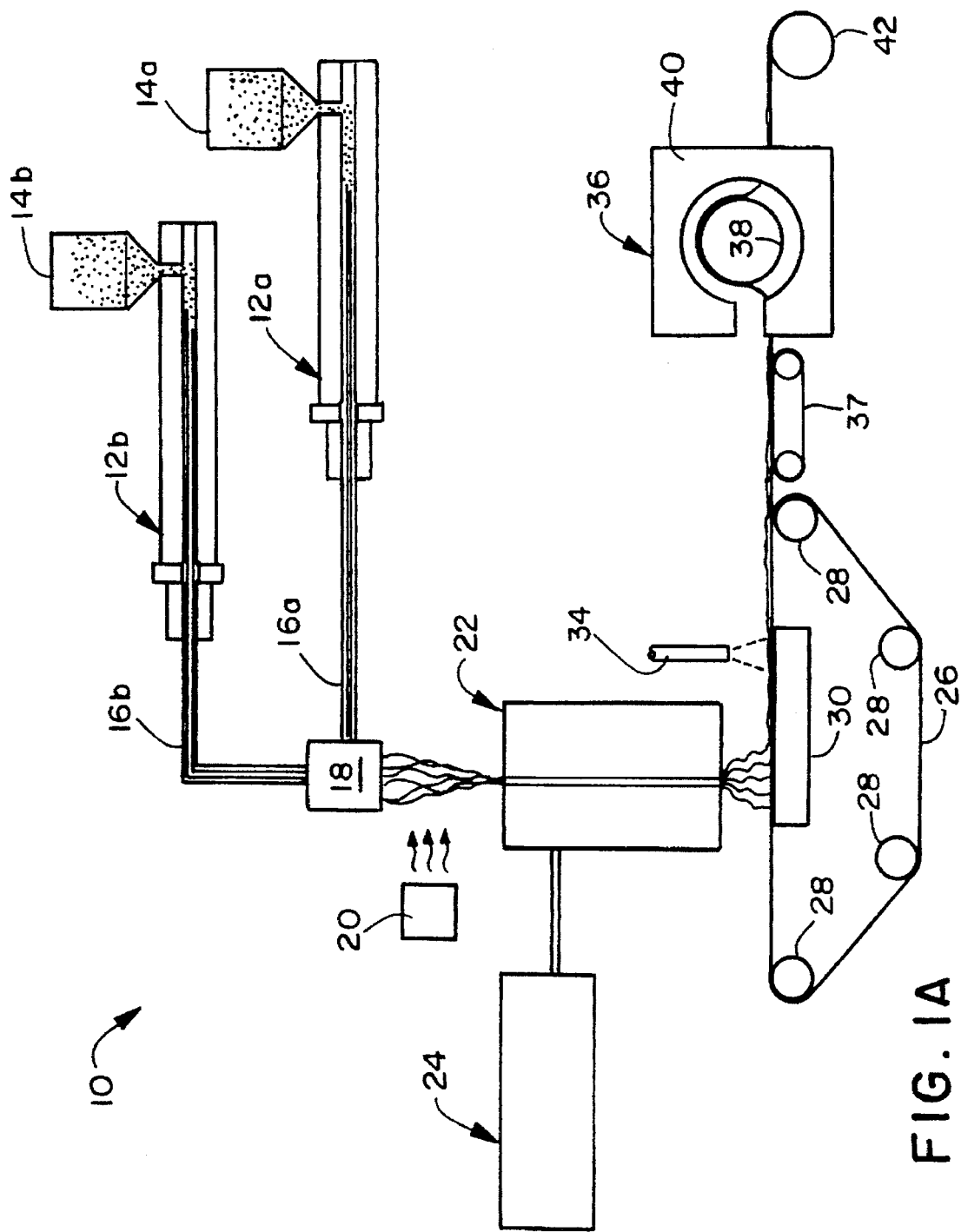
FIG. 1A is a schematic drawing of a process line for making an embodiment of the present invention.

Turning to FIG. 1A, a process line 10 for preparing a preferred embodiment of the present invention is disclosed. The process line 10 is arranged to produce bicomponent continuous filaments, but it should be understood that the present invention comprehends nonwoven fabrics made with multicomponent filaments having more than two components. For example, the fabric of the present invention can be made with filaments having three or four components.

The process line 10 includes a pair of extruders 12a and 12b for separately extruding the primary polymer component A and the adhesive polymer component B. Polymer component A is fed into the respective extruder 12a from a first hopper 14a and polymer component B is fed into the respective extruder 12b from a second hopper 14b. Polymer components A and B are fed from the extruders 12a and 12b through respective polymer conduits 16a and 16b to a spinneret 18. Spinnerets for extruding bicomponent filaments are well-known to those of ordinary skill in the art and thus are not described here in detail.

Generally described, the spinneret 18 includes a housing containing a spin pack which includes a plurality of plates stacked one on top of the other with a pattern of openings arranged to create flow paths for directing polymer components A and B separately through the spinneret. The spinneret 18 has openings arranged in one or more rows. The spinneret openings form a downwardly extending curtain of filaments when the polymers are extruded through the spinneret. For the purposes of the present invention, spinneret 18 may be arranged to form side-by-side or sheath/core bicomponent filaments illustrated in FIGS. 2A, 2B, and 2C.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1A, or both sides of the filament curtain.

A fiber draw unit or aspirator 22 is positioned below the spinneret 18 and receives the quenched filaments. Fiber draw units or aspirators for use in melt spinning polymers are well-known as discussed above. Suitable fiber draw units for use in the process of the present invention include a linear fiber aspirator of the type shown in U.S. Pat. No. 3,802,817 and eductive guns of the type shown in U.S. Pat. No. 3,692,618 and U.S. Pat. No. 3,423,266, the disclosures of which are incorporated herein by reference.

Generally described, the fiber draw unit 22 includes an elongate vertical passage through which the filaments are drawn by aspirating air entering from the sides of the passage and flowing downwardly through the passage. When it is desired to activate latent helical crimp in the filaments, heater 24 supplies hot aspirating air to the fiber draw unit 22. The hot aspirating air draws the filaments and ambient air through the fiber draw unit and activates the latent helical crimp.

A shaped, endless, at least partially foraminous, forming surface 26 is positioned below the fiber draw unit 22 and receives the continuous filaments from the outlet opening of the fiber draw unit. The forming surface 26 is a belt and travels around guide rollers 28. A vacuum 30 positioned below the forming surface 26 where the filaments are deposited draws the filaments against the forming surface. Although the forming surface 26 is shown as a belt in FIG. 1A, it should be understood that the forming surface can also be in other forms such as a drum. Details of particular shaped forming surfaces are explained below.

The process line 10 further includes one or more bonding devices such as the through-air bonders 34 and 36. Through-air bonders are well-known to those skilled in the art and are not disclosed here in detail. Generally described, the first through-air bonder 34 directs hot air through a nozzle against the filament web on the forming surface 26. Hot air from the nozzle of the first through-air bonder 34 flows through the web and the forming surface and bonds the filaments of the web together. The second through-air bonder 36 is a more conventional through-air bonder which includes a perforated roller 38, which receives the web, and a hood 40 surrounding the perforated roller. A conveyor 37 transfers the web from the forming surface to the second through-air bonder. Lastly, the process line 10 includes a winding roll 42 for taking up the finished fabric.

It should be understood, however, that other through-air bonding arrangements are suitable to practice the present invention. For example, when the forming surface is a belt, the forming surface can be routed directly through a more conventional through-air bonder instead of under the first through-air bonder 34 disclosed above. Alternatively, when the forming surface is a drum, the through-air bonder can be incorporated into the same drum so that the web is formed and bonded on the same drum.

To operate the process line 10, the hoppers 14a and 14b are filled with the respective polymer components A and B. Polymer components A and B are melted and extruded by the respective extruders 12a and 12b through polymer conduits 16a and 16b and the spinneret 18. Although the temperatures of the molten polymers vary depending on the polymers used, when polypropylene and polyethylene are used as primary component A and adhesive component B respectively, the preferred temperatures of the polymers range from about 370° to about 530° F. and preferably range from 400° to about 450° F.

As the extruded filaments extend below the spinneret 18, a stream of air from the quench blower 20 at least partially quenches the filaments to develop a latent helical crimp in the filaments. The quench air preferably flows in a direction substantially perpendicular to the length of the filaments at a temperature of about 45° to about 90° F. and a velocity from about 100 to about 400 feet per minute. The filaments must be quenched sufficiently before being collected on the forming surface 26 so that the filaments can be arranged by the forced air passing through the filaments and forming surface. Quenching the filaments reduces the tackiness of the filaments so that the filaments do not adhere to one another too tightly before being bonded and can be moved or arranged on the forming surface during collection of the filaments on the forming surface and formation of the web.

After quenching, the filaments are drawn into the vertical passage of the fiber draw unit 22 by a flow of hot air from the heater 24 through the fiber draw unit. The fiber draw unit is preferably positioned 30 to 60 inches below the bottom of the spinneret 18. When crimped filaments are desired, the temperature of the air supplied from the heater 24 is sufficient that, after some cooling due to mixing with cooler ambient air aspirated with the filaments, the air heats the filaments to a temperature required to activate the latent crimp. The temperature required to activate the latent crimp of most bicomponent filaments ranges from about 110° F. to a maximum temperature less than the melting point of the adhesive component. The temperature of the air from the heater 24 and thus the temperature to which the filaments are heated can be varied to achieve different levels of crimp. Generally, a higher air temperature produces a higher number of crimps. The ability to control the degree of crimp of the filaments is particularly advantageous because it allows one to change the resulting density, pore size distribution and drape of the fabric by simply adjusting the temperature of the air in the fiber draw unit.

Although the preferred method of carrying out the present invention includes contacting the multicomponent filaments with heated aspirating air, the present invention encompasses other methods of activating the latent helical crimp of the continuous filaments before the filaments are formed into a web. For example, the multicomponent filaments may be contacted with heated air after quenching but upstream of the aspirator. In addition, the multicomponent filaments may be contacted with heated air between the aspirator and the web forming surface. Furthermore, the filaments may be heated by methods other than heated air such as exposing the filaments to electromagnetic energy such as microwaves or infrared radiation.

The filaments are deposited through the outlet opening of the fiber draw unit 22 onto the shaped, traveling forming surface 26, and as the filaments are contacting the forming surface, the vacuum 20 draws the filaments against the forming surface to form an unbonded, nonwoven web of continuous filaments which assumes a shape corresponding to the shape of the forming surface. As discussed above, because the filaments are quenched, the filaments are not too tacky and the vacuum can move or arrange the filaments on the forming surface as the filaments are being collected on the forming surface and formed into the web. If the filaments are too tacky, the filaments stick to one another and cannot be arranged on the surface during formation of the web.

After the filaments are collected on the forming surface, the filaments are first bonded by the first through-air bonder 34 while the web is still on the forming surface 26 so that the web retains the shape imparted by the forming surface when the web is removed from the forming surface. The first through-air bonder 34 directs a flow of air having a temperature above the melting temperature of the adhesive component B through the web and forming surface. Preferably, the hot air contacts the web across the entire width of the web. The hot air melts the lower melting adhesive component B and thereby forms bonds between the bicomponent filaments to integrate the web. When polypropylene and polyethylene are used as polymer components A and B respectively, the air flowing from the first through-air bonder preferably has a temperature at the web surface ranging from about 230° to about 500° F. and a velocity at the web surface from about 1000 to about 5000 feet per minute. However, the temperature and velocity of the air from the first through air bonder 34 may vary depending on factors such as the polymers which form the filaments, the thickness of the web, the area of web surface contacted by the air flow, and the line speed of the forming surface. In addition, when a more conventional through-air bonder is substituted for the first through air-bonder 34, the air temperature and velocity will vary from that of the first through-air bonder.

After being bonded with the first through-air bonder 34, the fabric is transferred from the forming surface 26 to the second through-air bonder 36 with a conveyor 37 for more thorough bonding. In the second through-air bonder 36, air having a temperature above the melting temperature of adhesive component B is directed from the hood 40, through the web, and into the perforated roller 38. As with the first through-air bonder 34, the hot air in the second through-air bonder 36 melts the lower melting adhesive polymer component B and thereby forms bonds between the bicomponent filaments to integrate the web. When polypropylene and polyethylene are used as polymer components A and B respectively, the air flowing through the second through-air bonder preferably has a temperature ranging from about 230° to about 280° F. and a velocity from about 100 to about 500 feet per minute. The dwell time of the web in the second through-air bonder 36 is preferably less than about 6 seconds. It should be understood, however, that the parameters of the second through-air bonder 36 also depend on factors such as the type of polymers used and thickness of the web.

When used to make liquid absorbent articles, the fabric of the present invention may be treated with conventional surface treatments or contain conventional polymer additives to enhance the wettability of the fabric. For example, the fabric of the present invention may be treated with polyalkylene-oxide modified siloxanes and silanes such as polyalkylene-oxide modified polydimethyl-siloxane as disclosed in U.S. Pat. No. 5,057,361. Such a surface treatment enhances the wettability of the fabric. Lastly, the finished web is wound onto the winding roller 42 and is ready for further treatment or use.

When the spunbond filaments are crimped, the fabric of the present invention characteristically has a relatively high loft and is relatively resilient. The helical crimp of the filaments creates an open web structure with substantial void portions between filaments and the filaments are bonded at points of contact of the filaments.

Although the fabric described above is made with bicomponent filaments, it should be understood that the fabric of the present invention may be made with single component spunbond filaments. The single component spunbond filaments can be made in the same manner as described above with regard to FIG. 1A except that the spinneret is adapted to make single component filaments. The single component spunbond filaments have an average diameter from about 6 to about 40 microns, and preferably from about 15 to about 40 microns. The web is then bonded by adding the adhesive polymeric component in another manner.

One method of making the fabric of the present invention with single component spunbond filaments is to combine a polymeric bonder powder with the spunbond filaments during collection of the spunbond filaments on the forming surface and bond the filaments while the web is still on the forming surface.

Another suitable method of making the fabric of the present invention with single component spunbond filaments is to simultaneously spin spunbond adhesive filaments with the primary single component filaments. Another method is to combine single component staple length adhesive fibers with the primary spunbond filaments during collection of the primary spunbond filaments on the forming surface. With either of these methods, the web is then bonded in the same manner as the multicomponent filaments are bonded.

Still another method of making an embodiment of the present invention is to combine meltblown fibers with the spunbond continuous polymeric filaments. The meltblown fibers can contribute to bonding the spunbond filaments in two ways. According to one way, the spunbond filaments can be bonded after the web is separated from the forming surface. In such an embodiment, the spunbond filaments must be formed into a web which has sufficient integrity without adhesive bonding to be separated from the forming surface and then bonded without the surface features of the fabric disintegrating. This is accomplished by combining meltblown polymeric fibers with the spunbond filaments to form the web whereby the spunbond filaments and meltblown fibers are entangled sufficiently so that the array of surface features of the web remain intact during the separating and bonding steps. According to another way of bonding with meltblown fibers, the spunbond filaments can be bonded before or after the separation step. According to this method, adhesive meltblown fibers are combined with the spunbond continuous filaments and the resulting web is heated to activate the adhesive fibers.

Figure 1B:
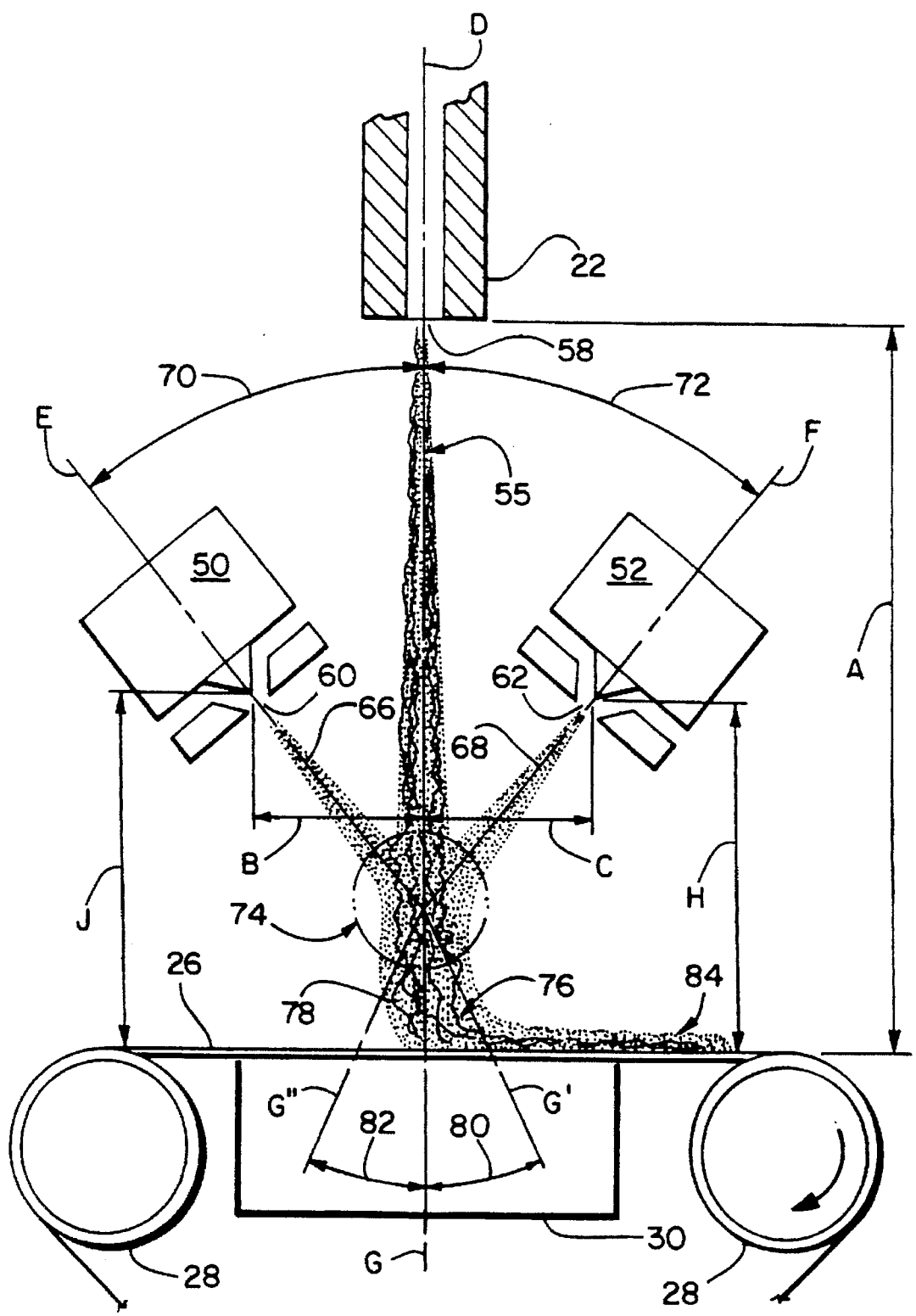
FIG. 1B is a schematic drawing of a process line for making another embodiment of the present invention.

Turning to FIG. 1B, there is shown a configuration for production of a preferred embodiment of the present invention by combining meltblown fibers with the spunbond filaments. Suitable meltblowing techniques are disclosed in U.S. Pat. No. 4,041,203, the disclosure of which is incorporated herein by reference. U.S. Pat. No. 4,041,203 references the following publications on meltblowing techniques which are also incorporated herein by reference: an article entitled "Superfine Thermoplastic Fibers" appearing in Industrial Engineering Chemistry, Volume 48, Number 8, ppgs. 1342–1346 which describes work done at the Naval Research Laboratories in Washington, D.C.; Naval Research Laboratory Report 111437, dated Apr. 15, 1954; U.S. Pat. No. 3,715,251; 3,704,198; 3,676,242; and U.S. Pat. No. 3,595,245; and British Specification Number 1,217,892.

FIG. 1B shows the spunbond web forming apparatus 10 of FIG. 1A except that meltblowing dies 50 and 52 are positioned on each side of the spunbond filament curtain 55 in a symmetric fashion. The aspirator 22 of the spunbond unit is positioned along a center plane D which plane defines the position of the spunbond filament curtain 55. The exit of 58 of the aspirator 22 is positioned at a distance A from the forming surface 26. This distance A is 20 inches or less and is called the spunbond forming height. The meltblowing dies 50 and 52 have die tips 60 and 62 respectively. The die tips 60 and 62 are spaced at equal distances B and C from the center plane D, respectively. The distance is B and C range from 0.5 to 7 inches with respect to the center plane D contained within the spunbond filament curtain 55. The meltblown die tips 60 and 62 are positioned above the forming surface 26 at distances J and H respectively. The meltblowing dies 50 and 52 generate air conveyed meltblown fiber curtains 66 and 68 which have center planes E and F respectively. These meltblown fiber curtains impinge the spunbond filament curtain 55 so that angles 70 and 72 formed between the respective center planes D and E and D and F, are equal. These angles 70 and 72 have values that range from 90° (for maximum impingement) to just less than 5° (for converging of the fibers in an almost laminar structure). The spunbond filaments and meltblown fibers integrate in mixing zone 74 to form a mixture of fibers 76 contained in a merged jet or curtain 78 that has a center plane G. The center plane G of the mixture of fibers 76 may deviate by an angle of 80 to position G' or by an angle 82 to position G" from the initial center plane D of the spunbond fiber curtain 55. Angles 80 and 82 may range from 0° up to 20°. The mixture of fibers 76 is then deposited on the forming surface 26. As with the apparatus shown in FIG. 1A, the deposition of fibers on the forming surface 26 is assisted by a vacuum 30 beneath the forming surface.

As discussed above, the combination of meltblown fibers with the spunbond filaments allows for bonding of the filaments after separation of the web from the forming surface. A sufficient amount of meltblown fibers must be added to provide enough entanglement of the spunbond filaments so that the web can be separated from the forming surface and then bonded while the surface features of the web remain intact. However, the meltblown fiber content of the web cannot be so high as to prevent movement of the spunbond filaments during collection and arrangement of the filaments on the forming surface. Otherwise, the spunbond filaments will not be able to take on a shape which corresponds to the forming surface. Also as discussed above, the meltblown fibers can be added as the adhesive component of the web to adhesively bond the spunbond filaments. To do so the meltblown polymer should have a lower melting point than the polymer which forms the spunbond filaments so that the filaments can be through-air bonded.

Figure 1C:
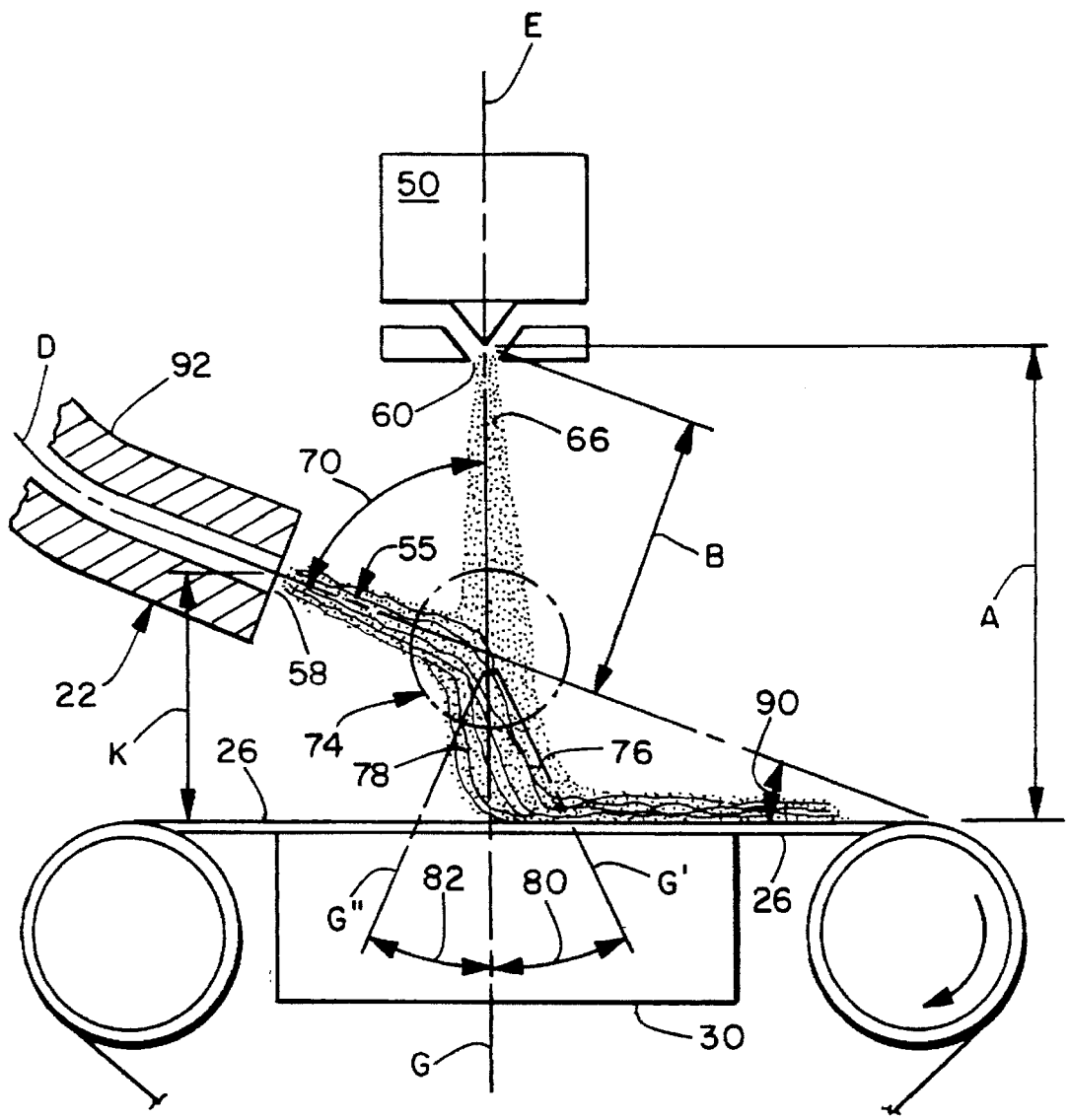
FIG. 1C is a schematic drawing of a process line for making another embodiment of the present invention.

Another configuration for production of an embodiment of the present invention is shown in FIG. 1C, and similar reference numerals and letters identify similar parts shown in FIGS. 1A, 1B and 1C. The configuration shown in FIG. 1C incorporates the features of FIG. 1B except that the spunbond filament curtain 55 and its center plane D are oriented at an acute angle 90 with respect to the forming surface 26 through the use of a curved section 92 adjacent the exit 58 of the spunbond aspirator 22. The meltblowing die 50 forms a meltblown fiber curtain 66 with a center line E. The meltblown die tip 60 is positioned above the spunbond filament curtain 55 so that the distance A between the meltblown die tip 60 and the forming surface 26 is less than 20 inches. The center plane D of the spunbond filament curtain 55 is positioned a distance B from the meltblown die tip 60. This distance B represents the shortest distance between center plane D and meltblown die tip 60 and ranges from 0.5 to 7 inches. The exit 58 of the spunbond aspirator is positioned above the forming surface 26 at a distance K. The meltblown fiber curtain 66 impinges the spunbond filament curtain 55 so that the angle 70 formed by the center planes D and E has a range from 90° (for maximum impingement) to just less than 5° (for converging of the fibers in an almost laminar structure). The spunbond filaments and meltblown fibers integrate in mixing zone 74 to form a mixture of fibers 76 contained in a merged jet or curtain 78 that has a center line G. The center line G of the mixture of fibers 76 may deviate by an angle 80 to positioned G' or by an angle 82 to position G" from the initial center line E of the meltblown fiber curtain 50. The angles 80 and 82 range from 0° up to 30°. The integrated spunbond filaments and meltblown fibers are deposited on a porous forming surface in the same manner as previously described. Because the meltblown fiber curtain 50 is traveling at a higher velocity than the spunbond filament curtain 55 and the introduction of the spunbond curtain is from the side of the meltblown fiber curtain 66 through the curved exit section 92, the deposition of the meltblown fibers and spunbond filaments on the forming surface 26 is more controlled than with the configuration shown in FIG. 1B wherein the high velocity meltblown fiber curtains are introduced from the sides of the spunbond curtain.

The forming surface 26 shown in FIGS. 1A and 1B may take on many configurations in the practice of the present invention. Generally described, the forming surface used with the present invention is shaped so that the forming surface has an array of discrete surface features. The surface features may be recesses or projections. The nonwoven web formed on the surface feature assumes a shape which corresponds to the shape of the forming surface. Thus, when the forming surface features are recesses, the resulting fabric has projections, and when the forming surface features are projections, the resulting fabric has apertures.

The surface features of the forming surfaces used to make the fabric of the present invention each have a cross-section extending between adjacent land areas and the cross-sections of at least some of the individual surface features of the forming surface have a minimum dimension of at least 0.03 inches. Thus, when nonwoven fabric is formed on such a forming surface the surface features of the fabric have the corresponding minimum dimension. For example, when the surface features of the forming surface include recesses, the forming surface has a length and a width which define a reference surface area and the recesses each have an open cross-sectional area which forms part of the reference surface area and extend between adjacent land areas. The open cross-sectional areas of the recesses preferably total from about 10 to about 95% of the reference surface area and more preferably from about 25 to about 50% of the reference surface area. The recesses preferably have a depth of at least about 0.05 inches. The cross-section of the recesses extending between the adjacent land areas more preferably has a minimum dimension of at least 0.05 inches.

Examples of a forming surface and a fabric made on that forming surface in accordance with a preferred embodiment of the present invention are shown in FIGS. 3A, 3B, 4A, and 4B. The forming surface 100 shown in FIG. 3A includes a rubber mat 102 adhered to a fine mesh support wire 104. The rubber mat is stamped with a pattern of rectangular shaped apertures which form an array of rectangular shaped recesses 106 in the forming surface 100. The recesses 106 are open on one side and bounded on the other side by the support wire 104. If the depth of the recesses is sufficient so that the filaments do not extend through the bottom side of the rubber mat and the rubber mat is sufficiently stiff to maintain a level forming surface, the support wire can be eliminated.

The rubber mat can be made of a rubber with a melting point greater than the temperature of the hot air used to bond the fabric web on top of the forming surface. Suitable rubbers include silicone rubber, ethylene propylene diene modified rubber, and the like. The rubber mat 102 is adhered to the foraminous support wire with a suitable adhesive.

Figure 3A:
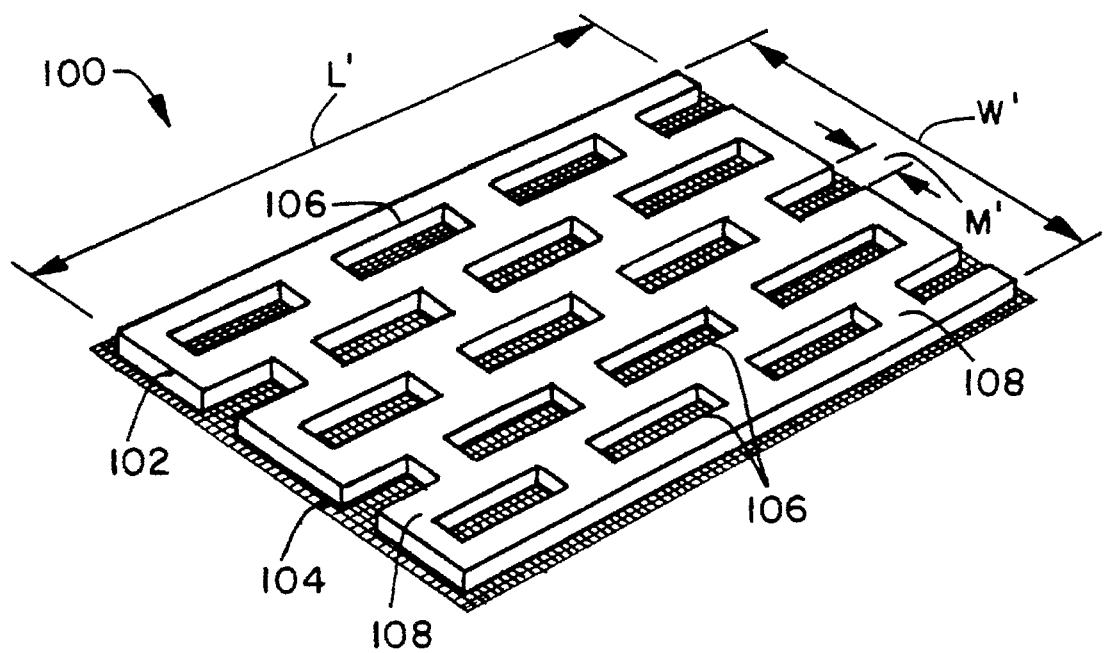
FIG. 3A is partial perspective view of a forming surface for making an embodiment of the present invention.
Figure 3B:
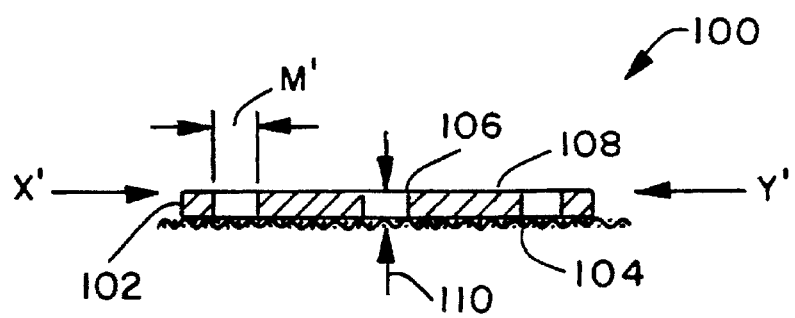
FIG. 3B is cross-sectional elevation view of the forming surface shown in FIG. 3A.
Figure 4A:
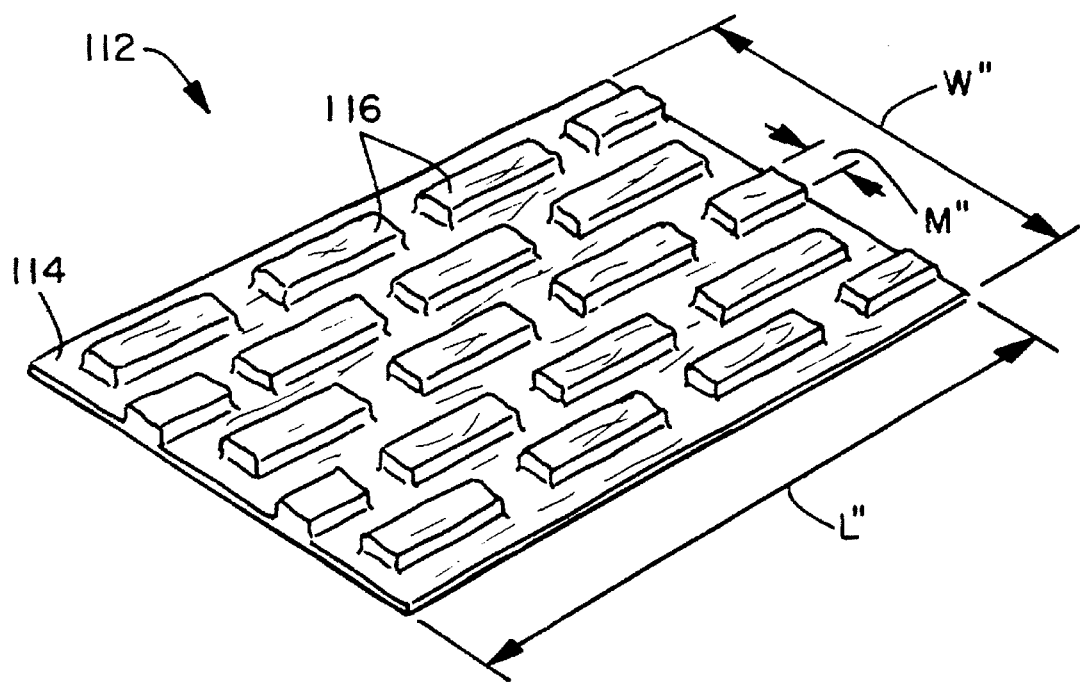
FIG. 4A is a partial perspective view of a fabric made using the forming surface shown in FIG. 3A.
Figure 4B:
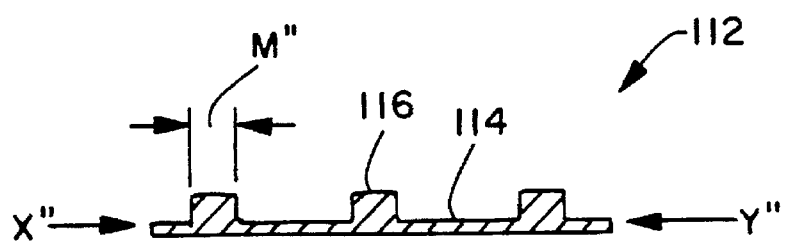
FIG. 4B is cross-sectional elevation view of the fabric shown in FIG. 4A.

The recesses 106 in the forming surface 100 are separated by land areas 108. The forming surface 100 has a reference surface area defined by the length L' and the width W'. The reference surface area lies in the plane between the arrows X' and Y' shown in FIG. 3B. The recesses 106 have a cross-section which extends between adjacent land areas 108 and forms part of the reference surface area. The recesses have a minimum dimension of M' as shown in FIGS. 3A and 3B. It is this minimum dimension M' that is preferably at least about 0.05 inches. The recesses 106 also have a depth 110 of at least about 0.05 inches.

To form a fabric with a nonuniform basis weight, the land areas 108 of the forming surface 100 are less air permeable than the recesses. Preferably, the land areas 108 are nonporous and the recesses 106, being open except for the forming wire underneath, are foraminous. As a result, when the fabric is formed on top of the forming surface 100, the continuous filaments are drawn by the vacuum beneath the forming surface into the recesses 106 because the pressure drop across the recesses is less than the pressure drop across the land areas. Thus, the resulting fabric 112 shown in FIGS. 4A and 4B has a shape which corresponds to the shape of the forming surface 100 and the fabric projections are substantially filled with filaments which means that the side of the fabric opposite the projections is substantially planar and does not have indentions or recesses which extend into the projections. Like the forming surface 100, the fabric 112 produced thereon includes land areas 114. The land areas 114 of the fabric 112 correspond to the land areas 108 of the forming surface 100. The fabric 112 also includes projections 116 formed in the recesses 106 of the forming surface 100. The projections 116 are separated by the land areas 114 of the fabric. Because the filaments of the fabric 112 are drawn into the recesses 106 of the forming surface 100 during formation of the web, the projections 116 of the fabric have a higher basis weight than the adjacent land areas 114. Preferably, the projections have a basis weight which is at least about 30% greater than the basis weight of the land areas.

Like the forming surface 100, the fabric 112 has a reference surface area defined by the length L" and width W" of the fabric. This reference surface area lies on the plane extending between the arrows X" and Y" shown in FIG. 4B. The projections 116 and the fabric 112 each have a cross-sectional area which extends between adjacent land areas 114 and forms a part of the reference surface area of the fabric. The projections 116 of the fabric 112 have a minimal dimension M" which is at least about 0.05 inches. Like the forming surface 100, the cross-sectional areas of the projections 116 of the fabric 112 preferably total from about 10 to about 95% of the referenced surface area of the fabric, and more preferably from about 25 to about 50% of the reference surface area of the fabric.

Figure 5:
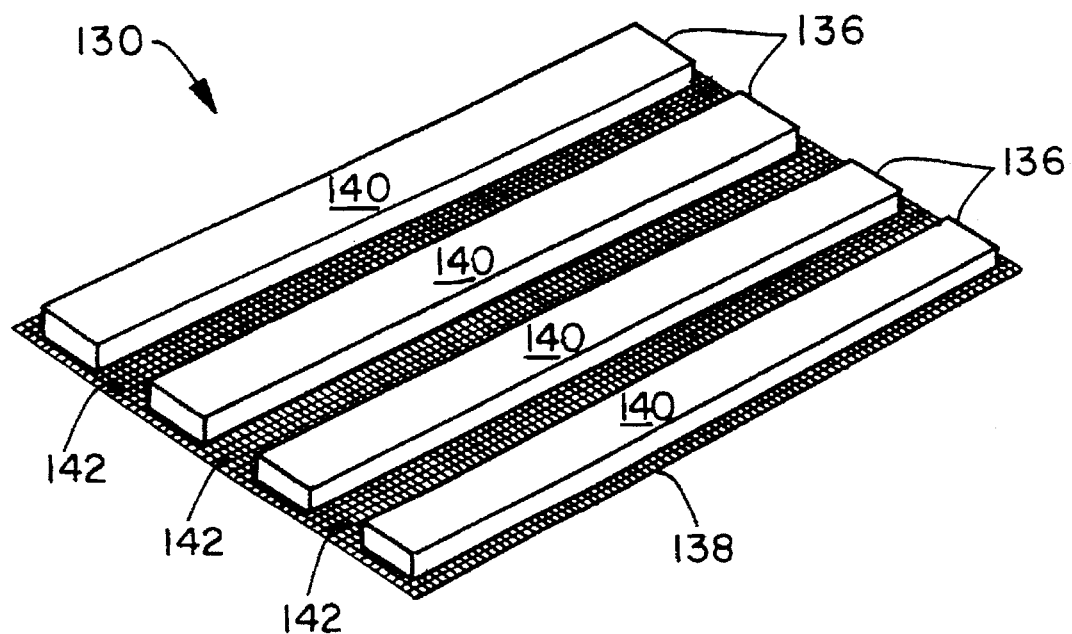
FIG. 5 is a partial perspective view of a forming surface for making another embodiment of the present invention.
Figure 6:
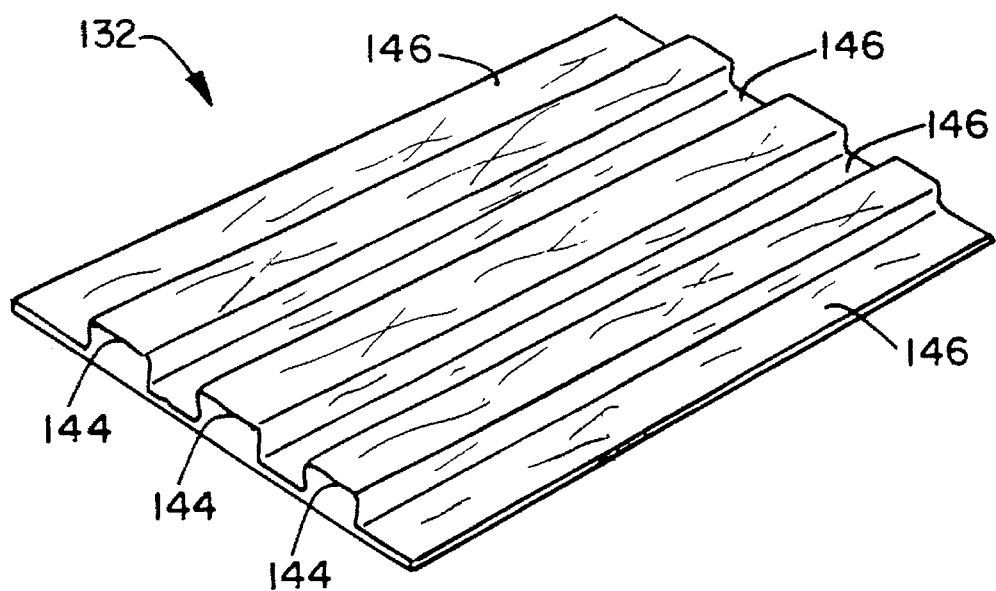
FIG. 6 is a partial perspective view of a fabric made using the forming surface shown in FIG. 5.

Another forming surface 130 for making another embodiment of the present invention is shown in FIG. 5 and the fabric 132 made on that forming surface is shown in FIG. 6. The forming surface 130 comprises a plurality of spaced, parallel strips of rubber 136 adhered to a foraminous support wire 138. The spaced rubber strips 136 form land areas 140 and channel-shaped recesses 142 therebetween. Preferably, the rubber strips 140 are non-porous and the channel-shaped recesses 142 are foraminous because the support wire 138 is exposed between the rubber strips, but, as with the previous embodiment, the land areas can have some degree of air permeability as long as the air permeability of the recesses is greater than the air permeability of the land areas.

As with the forming surface shown in FIG. 3A, when the fabric 132 is formed on the forming surface 130, the continuous filaments are drawn into the recesses 142 by the vacuum beneath the forming surface 130. As a result, the fabric 132 includes projections 144 which correspond to the recesses 142 in the forming surface 130 and land areas 146 which correspond to the land areas 140 on the forming surface. The projections 144 are substantially fried with filaments.

Figure 7:
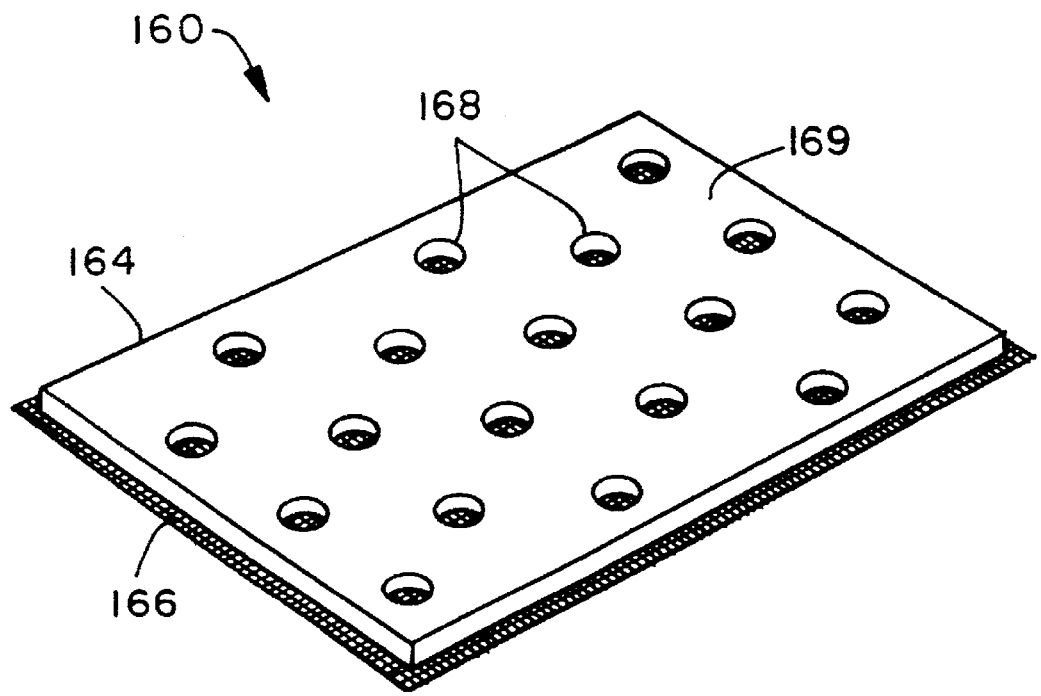
FIG. 7 is a partial perspective view of a forming surface for making still another embodiment of the present invention.
Figure 8:
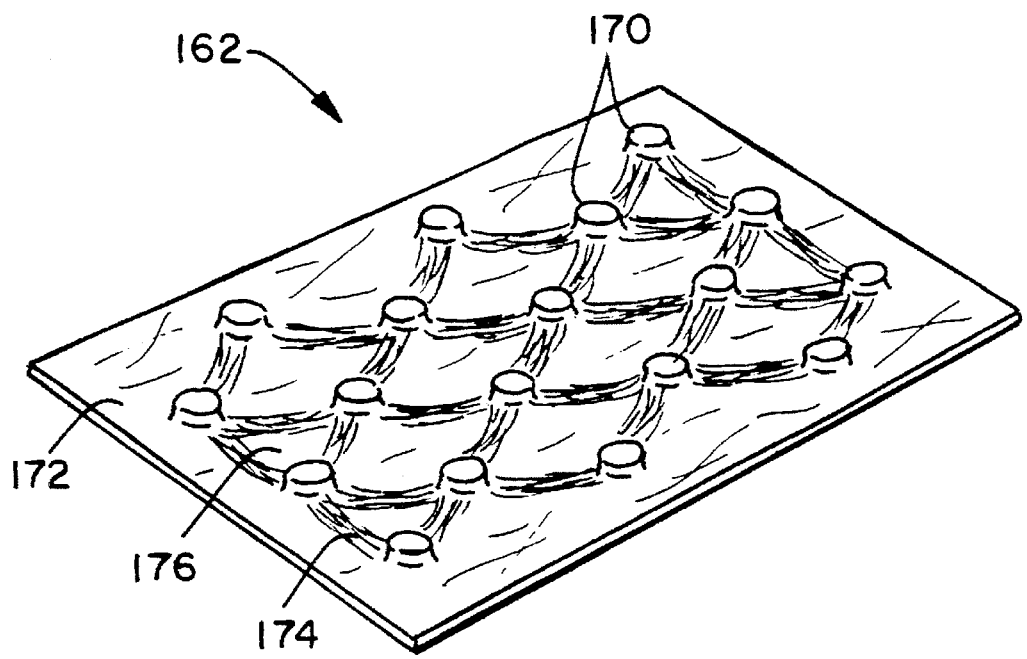
FIG. 8 is a partial perspective view of a fabric made with the forming surface shown in FIG. 7.

Still another forming surface 160 is shown in FIG. 7 and a fabric 162 made on that forming surface is shown in FIG. 8. This forming surface includes a nonporous rubber mat 164 adhered to a foraminous support wire 166. Holes are punched into the rubber mat 164 to form an array of foraminous recesses 168 in the forming surface 160. The recesses 168 are circular in cross-section.

When the nonwoven fabric 162 is made on the forming surface 160, the continuous spunbond filaments are drawn into the circular recesses 168 of the forming surface 160. The resulting fabric has an array of projections 170 separated by land areas 172. The projections 170 correspond to the circular recesses 168 in the forming surface 160 and the land areas 172 correspond to the land areas 169 of the forming surface. Again, the projections 170 are substantially filled with filaments. The fabric 162 shown in FIG. 8 illustrates the structural heterogeneity of spunbond fabric which can be made by the present invention. As explained in the summary above, the process of the present invention can make fabric with zones of different liquid handling properties. More specifically, the process of the present invention can control the ability of the resulting fabric to direct flow along all three dimensions of the fabric—along, along the length of the fabric coplanar with the land areas, along the width of the fabric coplanar with the land areas, and through the thickness or depth of the fabric. These zones of different liquid handling ability are created by areas of different basis weight and density and filament orientation.

In the embodiment shown in FIG. 8, the basis weight of the fabric projections 170 is greater than the basis weight of the adjacent land areas 172, because the spunbond filaments of the fabric 162 are drawn into the recesses 168 of the forming surface 160 and the resulting fabric projections are substantially filled with filaments. In addition, as the filaments are drawn into the recesses 168 of the forming surface 160, some filaments become aligned into bundles 174 connecting the projections 170. The bundles 174 have a higher density than adjacent lower density areas 176 of the land areas 172. The filaments in the bundles 174 tend to be unidirectionally oriented in the plane of the land areas 172 and the filaments in the projections 170 tend to be multidirectionally oriented with enhanced directionality along the depth of the projections. The difference in basis weight between the land areas 172 and the projections 170 and the degree of orientation of the filaments can be increased by increasing the flow and pressure of the air pulled by the vacuum 30 beneath the forming surface 160 and can also be controlled by manipulating the size, shape, and spacing of the recesses 168 in the forming surface 160. In addition, the orientation of the filaments into bundles 174 between the projections can be manipulated by forming grooves in the forming surface 160 between the recesses 168. Furthermore, the liquid handling properties of the fabric 162 are also affected by a density gradient in the fabric projections. Because the flow of air through the filaments during formation of the fabric 162 decreases as the filaments build u$_i$, on the forming surface, the filaments tend to be more dense towards the forming surface 160 and the support wire. This effect can be controlled by manipulating the vacuum during formation and the depth of the recesses 168.

When the fabric 162 is used as an absorbent article, the lower density zones 176 of the land areas 172 are suitable for fluid intake, the higher density zones 174 of the land areas are suitable for wicking fluid across the land areas between the projections 170 extending from the fabric, and the projections extending from the fabric are useful for liquid collection and transfer through the depth of the fabric, and separation of the fabric from an adjacent surface.

Although the forming surfaces described above include rubber mats or strips attached to a wire mesh support, there are other methods of making such forming surfaces. For example, the entire forming surface can be made of shaped metal forming wire with the land areas made non-porous by sealing with a material such as rubber or latex paint. In addition, the forming surface can be made by thermoforming a plastic wire mesh such as a polyester wire mesh into a configuration wherein the mesh has an array of projections separated by land areas. Likewise, the land areas can be made non-porous by sealing with a material such as rubber or latex paint.

When it is desired to make an apertured nonwoven fabric, the surface features of the forming surface include non-porous projections separated by foraminous areas. The projections have a shape so that, during the step of forcing air through the web of the forming surface, the filaments are drawn along the projections towards the land areas of the forming surface, so that the corresponding surface features of the fabric include apertures which correspond to the shape of the cross-section of the projections. The projections of the forming surface each have a cross-section extending between adjacent foraminous land areas and the cross-sections of at least some of the individual projections of the forming surface have a minimum dimension of at least 0.03 inches. Preferably, the forming surface has a length and a width defining a reference surface area which includes the foraminous land areas and the cross-sections of the projections extending between the land areas. The projections extend from the reference surface area and the cross-sectional areas of the projections total from about 10 to about 95% of the reference surface area. The projections preferably have a height of at least about 0.10 inches and have a smooth outer surface and a sharply pointed apex. A more net-like fabric can be made with a forming surface having relatively larger and closely spaced projections, a more cloth-like fabric can be made with a forming surface having relatively smaller and more closely spaced projections, and a separation layer material can be made with a forming surface having a relatively small number of widely spaced projections.

Figure 9A:
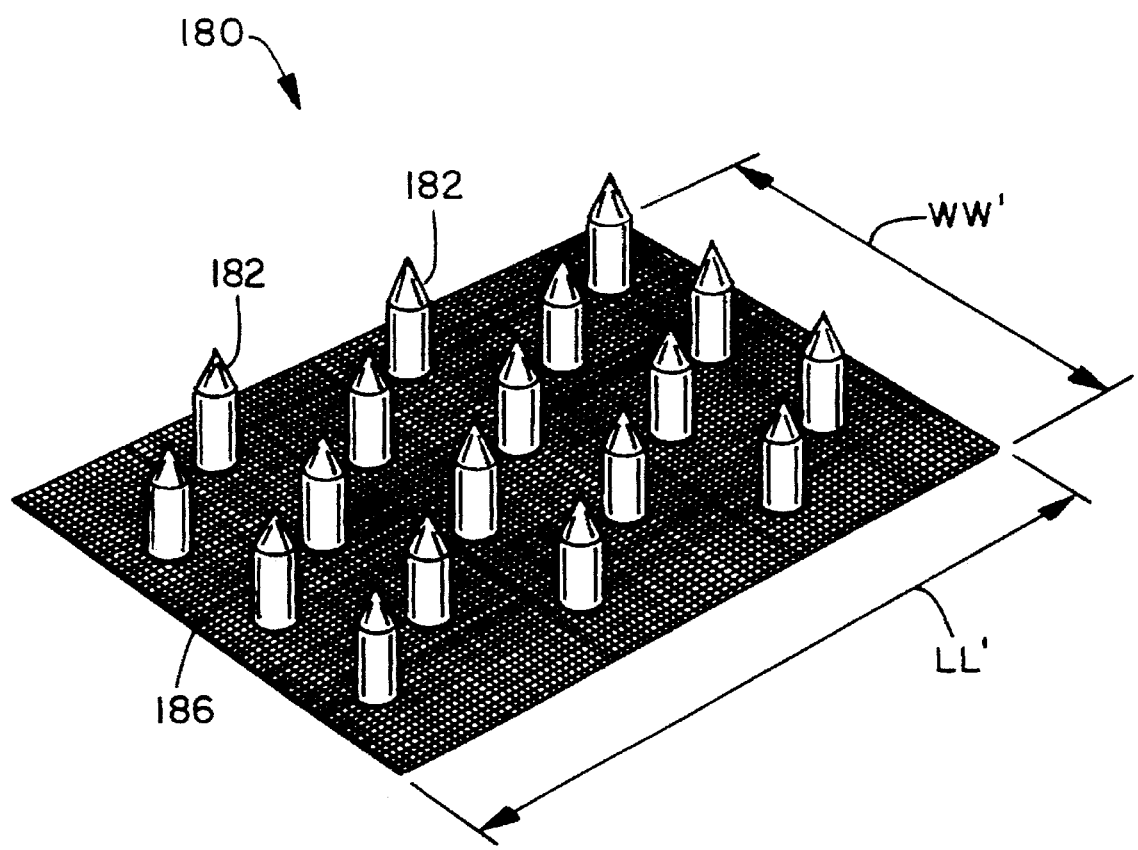
FIG. 9A is a partial perspective view of a forming surface for making yet another embodiment of the present invention.
Figure 10A:
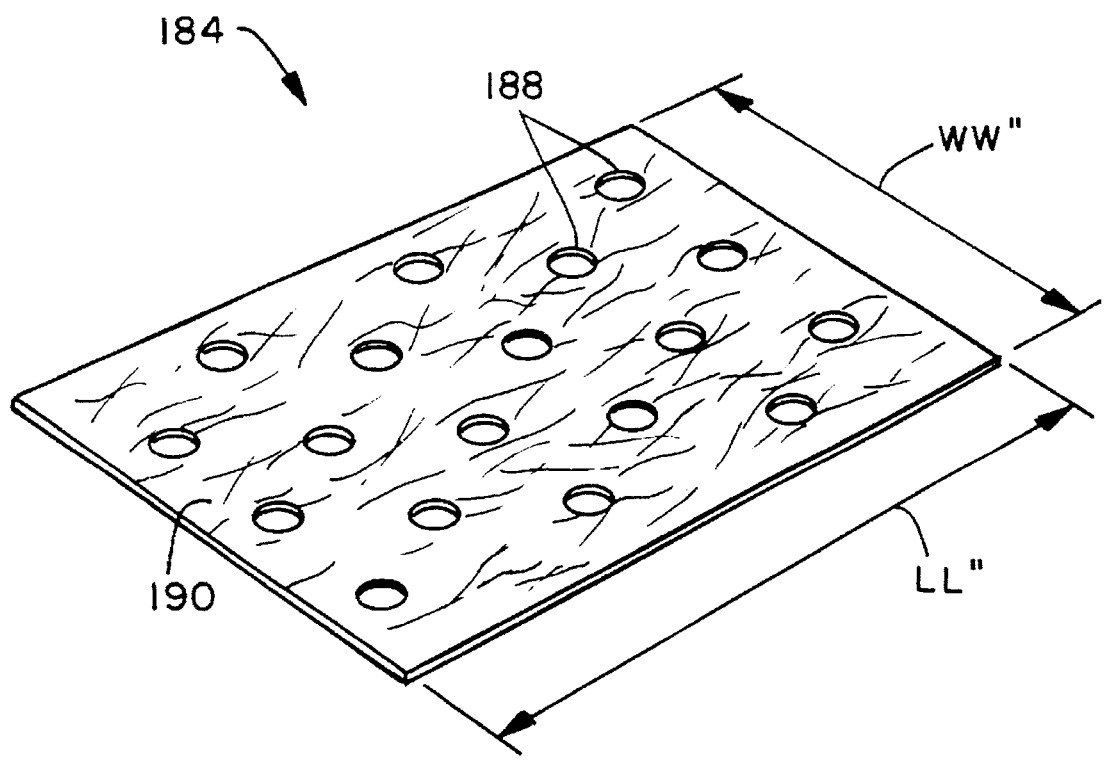
FIG. 10A is a partial perspective view of a fabric made using the forming surface shown in FIG. 9A.

An example of a forming surface 180 with projections 182 and a fabric 184 made with that forming surface are shown in FIGS. 9A and 10A. The forming surface 180 comprises an array of projections 182 protruding from a foraminous forming wire 186. The forming wire 186 forms the land areas of the forming surface 180. The projections 182 are smooth, non-porous metal pins with sharply pointed apexes. During formation of the fabric 184 on the forming surface 180, the continuous filaments are drawn down along the projections 182 to the land areas 186. As a result, the fabric 194 is substantially planer and has an array of apertures 188 separated by land areas 190.

Figure 9B:
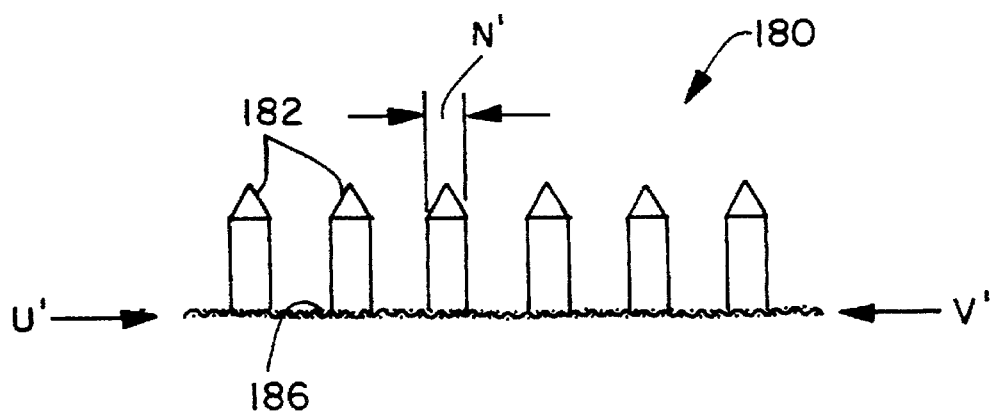
FIG. 9B is cross-sectional elevation view of the forming surface shown in FIG. 9A.

The forming surface 180 has a reference surface area defined by the length LL' and width WW' of the forming surface. The reference surface area includes the land areas 186 of the forming surface and the cross-sections of the projections 182. The reference surface area of the forming surface lies in the plane between the arrows U' and V' shown in FIG. 9B. The projections 182 have a minimum dimension N' which is at least about 0.03 inches.

Figure 10B:
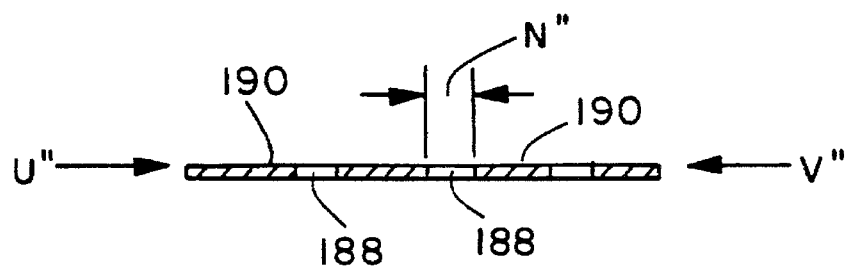
FIG. 10B is cross-sectional elevation view of the fabric shown in FIG. 10A.

Likewise, the fabric 184 produced on the forming surface 180 has a reference surface area defined by the length LL" and width WW" of the fabric. The reference surface area of the fabric 184 lies in the plane between the arrows U" and V" shown in FIG. 10B. The reference surface area of the fabric 184 includes the land areas 190 of the fabric and the open cross-sectional areas of the apertures 188 extending between the land areas. The apertures 188 have cross-sectional areas with a minimum dimension N" which is at least about 0.03 inches. The dimensions of the apertures 188 of the fabric 184 correspond to the dimensions of the projections 182 of the forming surface 180.

Although the forming surface 180 shown in FIG. 9A includes pins 182 protruding through a wire mesh 186, the forming surface can also be made with shaped metal wire mesh or polyester mesh as described above with regard to forming surfaces having recesses. However, in this case, the wire projections are made nonporous by sealing with a material such as rubber or latex paint and the land areas are left open.

The following examples are designed to illustrate particular embodiments of the present invention and teach one of ordinary skill in the art how to carry out the present invention.

EXAMPLE 1

A nonwoven fabric web comprising continuous bicomponent filaments is made with the process illustrated in FIG. 1A and described above. The configuration of the filaments was side-by-side, the weight ratio of one side to the other being 1:1. The spin hole geometry was 0.6 mm diameter with an L/D ratio of 4:1 and the spinneret had 50 openings per inch in the cross-machine direction. The composition of the primary component A was 98% by weight 3445 polypropylene from Exxon of Houston, Tex. and 2% by weight titanium dioxide. The composition of adhesive component B was 98% by weight ASPUN 6811A linear low density polyethylene from Dow Chemical Company of Midland, Mich. and 2% by weight titanium dioxide. The melt temperature in the spin pack was 440° F. and the spin hole throughput was 0.7 ghm(grams/hole/minute). The forming height was 10 inches. The quench air flow rate was 32 scfm and the quench air temperature was 53° F. The aspirator feed temperature was 350° F. and the aspirator air exit temperature was 220° F. The aspirator manifold pressure was 3.6 psi. The temperature of the air flow exiting the first through-air bonder was 450° at the first through-air bonder and 350° F. at the web. The under-wire vacuum was 15 in. $H_2O$. The temperature of the heated air in the second through-air bonder was 255° F. and the second through-air bonder air pressure differential between the hood and the perforated roll was 0.7 in. $H_2O$. The forming surface was of the type shown in FIG. 3A and comprised a 1/8 inch thick ethylene propylene diamine modified sheet stamped with the pattern of rectangular recesses. Each recess was 3/16 inches wide and 3/4 inches long, and spaced end-to-end 3/16 inches apart. The lines of recesses were spaced 3/8 inches apart side-to-side. The rubber sheet was attached to a continuous polyester support wire.

EXAMPLE 2

A nonwoven fabric web comprising continuous bicomponent filaments is made with the process illustrated in FIG. 1A and described above. The configuration of the filaments was side-by-side, the weight ratio of one side to the other being 1:1. The spin hole geometry was 0.6 mm diameter with an L/D ratio of 4:1 and the spinneret had 50 openings per inch in the cross-machine direction. The composition of the primary component A was 98% by weight 3445 polypropylene from Exxon of Houston, Tex. and 2% by weight titanium dioxide. The composition of adhesive component B was 98% by weight ASPUN 6811A linear low density polyethylene from Dow Chemical Company from Midland, Mich. and 2% by weight titanium dioxide. The melt temperature in the spin pack was 440° F. and the spin hole throughput was 0.7 ghm. The forming height was 7.5 inches. The quench air flow rate was 32 scfm and the quench air temperature was 53° F. The aspirator feed temperature was 350° F. and the aspirator air exit temperature was 220° F. The aspirator manifold pressure was 5.0 psi. The temperature of the air flow exiting the first through-air bonder was 450° at the first through-air bonder and 350° F. at the web. The under-wire vacuum was 17 in. $H_2O$. The temperature of the heated air in the second through-air bonder was 255° F. and the second through-air bonder air pressure differential between the hood and the perforated roll was 0.7 in. $H_2O$. The forming surface was of the type shown in FIG. 3A and comprised a 1/8 inch thick ethylene propylene diamine modified sheet stamped with the pattern of rectangular recesses. Each recess was 3/16 inches wide and 3/4 inches long, and spaced end-to-end 3/16 apart. The lines of recesses were spaced 3/16 inches apart side-to-side. The rubber sheet was attached to a continuous polyester support wire.

EXAMPLE 3

A nonwoven fabric web comprising continuous bicomponent filaments is made with the process illustrated in FIG. 1A and described above. The configuration of the filaments was side-by-side, the weight ratio of one side to the other being 1:1. The spin hole geometry was 0.6 mm in diameter with an L/D ratio of 4:1 and the spinneret had 50 openings per inch in the cross-machine direction. The composition of the primary component A was 98% by weight 3445 polypropylene from Exxon of Houston, Tex. and 2% by weight titanium dioxide. The composition of adhesive component B was 98% by weight ASPUN 6811A linear low density polyethylene from Dow Chemical Company from Midland, Mich. and 2% by weight titanium dioxide. The melt temperature in the spin pack was 400° F. and the spin hole throughput was 0.6 ghm. The forming height was 5.5 inches. The quench air flow rate was 32 scfm and the quench air temperature was 53° F. The aspirator feed temperature was 350° F. and the aspirator air exit temperature was 220° F. The aspirator manifold pressure was 5.0 psi. The temperature of the air flow exiting the first through-air bonder was 450° at the first through-air bonder and 350° F. at the web. The under-wire vacuum was 17 in. $H_2O$. The temperature of the heated air in the second through-air bonder was 255° F. and the second through-air bonder air pressure differential between the hood and the perforated roll was 0.7 in. $H_2O$. The forming surface was of the type shown in FIG. 3A and comprised a 1/8 inch thick ethylene propylene C-mine modified sheet stamped with the pattern of rectangular recesses. Each recess was 3/16 inches wide and 3/4 inches long, and spaced end-to-end 3/16 apart. The lines of recesses were spaced 3/8 inches apart side-to-side. The rubber sheet was attached to a continuous polyester support wire.

EXAMPLE 4

A nonwoven fabric web comprising continuous bicomponent filaments is made with the process illustrated in FIG. 1A and described above. The configuration of the filaments was side-by-side, the weight ratio of one side to the other being 1:1. The spin hole geometry was 0.6 mm diameter with an L/D ratio of 4:1 and the spinneret had 50 openings per inch in the cross-machine direction. The composition of the primary component A was 98% by weight 3445 polypropylene from Exxon of Houston, Tex. and 2% by weight titanium dioxide. The composition of adhesive component B was 98% by weight ASPUN 6811A linear low density polyethylene from Dow Chemical Company from Midland, Mich. and 2% by weight titanium dioxide. The melt temperature in the spin pack was 440° F., the spin hole throughput was 0.7 ghm. The forming height was 10 inches. The quench air flow rate was 32 scfm and the quench air temperature was 53° F. The aspirator feed temperature was 350° F. and the aspirator air exit temperature was 220° F. The aspirator manifold pressure was 3.5 psi. The temperature of the air flow exiting the first through-air bonder was 450° at the first through-air bonder and 350° F. at the web. The under-wire vacuum was 15 in. $H_2O$. The temperature of the heated air in the second through-air bonder was 255° F.

and the second through-air bonder air pressure differential between the hood and the perforated roll was 0.7 in. H$_2$O. The forming surface was of the type shown in FIG. 5 and comprised ¼ inch thick silicone rubber strips attached lengthwise to a 30 mesh stainless steel support wire and spaced ¼ inch apart.

Fabric samples from Examples 1–4 were analyzed and the results are shown in Table 1. As can be seen, the basis weight of the fabrics varied. The basis weight of the projections was significantly greater than the basis weight of the land areas. The basis weight was determined by dividing the weight of the fabric by the respective occupied area in the plane of the fabric. For example, the basis weight of the projections was determined by dividing the weight of the projections by the cross-sectional area of the projections in the plane of the fabric.

TABLE 1

| Example: | 1 | 2 | 3 | 4 |
|---|---|---|---|---|
| Denier (dpf) | 3.0 | 2.5 | 2.5 | 3.2 |
| Crimp level | high | med. | low | high |
| Basis Weight (osy) | | | | |
| Total | 1.63 | 1.72 | 1.72 | 2.82 |
| Projections | 4.30 | 2.48 | 4.54 | 4.12 |
| Land Areas | 0.86 | 0.96 | 0.99 | 1.70 |
| Caliper (mils) | | | | |
| Total | 57 | 51 | 54 | 227 |
| Projections | 57 | 51 | 54 | 227 |
| Land Areas | 32 | 26 | 30 | 63 |
| Density (g/cc) | | | | |
| Projections | 0.101 | 0.065 | 0.112 | 0.024 |
| Land Areas | 0.036 | 0.049 | 0.044 | 0.036 |

EXAMPLE 5

A nonwoven fabric web comprising continuous bicomponent filaments is made with the process illustrated in FIG. 1A and described above. The configuration of the filaments was concentric sheath/core, the weight ratio of sheath to core being 1:1. The spin hole geometry was 0.6 mm in diameter with an L/D ratio of 4:1 and the spinneret had 50 openings per inch in the cross-machine direction. The composition of the primary component A was 100% by weight 3445 polypropylene from Exxon of Houston, Tex. The composition of adhesive component B was 100% by weight ASPUN 6811A linear low density polyethylene from Dow Chemical Company from Midland, Mich. The melt temperature in the spin pack was 430° F., the spin hole throughput was 0.8 ghm. The forming height was 7.25 inches. The quench air flow rate was 20 scfm and the quench air temperature was 60° F. The aspirator feed was ambient air. The aspirator manifold pressure was 3.0 psi. The web was initially compressed with a heated roll instead of the first through-air bonder. The under-wire vacuum was 4 in. H$_2$O. The temperature of the heated air in the second through-air bonder was 260° F. The forming surface was of the type shown in FIG. 7 and comprised a 1/16 inch thick metal sheet stamped with the pattern of circular recesses. Each recess had a diameter of 3/16. The metal sheet was attached to a continuous polyester support wire. The resulting fabric had a structure like that illustrated in FIG. 8 with bundles of aligned filaments connecting the projections and land areas of lower basis weight between the bundles.

EXAMPLE 6

A nonwoven fabric web comprising continuous bicomponent filaments is made with the process illustrated in FIG. 1A and described above. The configuration of the filaments was side-by-side, the weight ratio of one side to the other being 1:1. The spin hole geometry was 0.6 mm in diameter with an L/D ratio of 4:1 and the spinneret had 50 openings per inch in the cross-machine direction. The composition of the primary component A was 98% by weight 3445 polypropylene from Exxon of Houston, Tex. and 2% by weight titanium dioxide. The composition of adhesive component B was 98% by weight ASPUN 6811A linear low density polyethylene from Dow Chemical Company from Midland, Mich. and 2% by weight titanium dioxide. The melt temperature in the spin pack was 430° F. and the spin hole throughput was 0.70 ghm. The forming height was 9 ⅝ inches. The quench air flow rate was 30 scfm and the quench air temperature was 56° F. The aspirator feed temperature was 350° F. and the aspirator air exit temperature was 220° F. The aspirator manifold pressure was 3.4 psi. The temperature of the air flow exiting the first through-air bonder was 410 at the first through-air bonder and approximately 330° F. at the web. The under wire vacuum was 9 in. H$_2$O. The temperature of the heated air in the second through-air bonder was 259° F. and the second through-air bonder air pressure differential between the hood and the perforated roll was 0.7 in. H$_2$O. The forming surface was of the type shown in FIG. 9A and comprised an array of ⅛ inch diameter polished nails protruding through a continuous polyester support wire and extending ½ inch above the forming surface. The resulting fabric had an array of apertures corresponding to the array of nails.

EXAMPLE 7

A nonwoven fabric web comprising continuous spunbond filaments and meltblown fibers was made with the process illustrated in FIG. 1B. The spunbond filaments were trilobal and comprised 100% by weight PD-3445 polypropylene from Exxon Chemicals Corporation of Houston, Tex. The spin hole through-put was 0.45 ghm and the attenuation force was sufficient to achieve final effective diameters for the spunbonded filaments between 20 and 30 microns.

Referring to FIG. 1B, the meltblown die tips 60 and 62, the exit 58 of the spunbond drawing apparatus 22 and the porous forming surface 26 used for this example are as follows: the forming height (A) was 17 inches, the distance from tip 60 to the spunbond filament curtain (B) was 7 inches, the distance from the tip 62 to the spunbond filament curtain (C) was 7 inches, the distance from tips 60 and 62 to the forming surface 26 (J and H) was 11 inches and the angles of tips 60 and 62 (70 and 72) was 45°.

The meltblown fibers were formed from molten polyethylene consisting of a 50/50 blend by weight of ASPUN 6814 from Dow Chemical Company of Midland, Mich. and NA-601-04 from Quantum Chemical, USI Division of Cincinnati, Ohio. Molten polyethylene was extruded at 425° F. through the meltblown tips at a rate of 0.44 pounds of polymer per inch of die tip length per hour (PIH). The attenuation forces on the extruded polymer were varied by controlling the volume metric flow of hot air (heated between 550°–600° F.) impinged on the molten polyethylene extruded through the capillaries of the tip. Meltblown fibers were formed that had diameters of 4–6microns. The meltblown fibers from the meltblowing die tips 60 and 62 were propelled in meltblown fiber curtains by the expanding and decelerating jets of air (used to attenuate them in molten form) towards the spunbond filament curtain and were combined with the spunbond filaments at a height of approximately 4 inches above the forming surface. The spunbond filaments were also being propelled towards the forming surface in a spunbond filament curtain by an expanding and decelerating jet of air (initially used to impart attenuation). The mixing of these fiber curtains carrying the respective fibers above the forming surface resulted in a distribution of meltblown fibers through the spunbond filaments in a combined fiber curtain that was then propelled toward the porous forming surface.

The vacuum below the forming surface caused air to pass through the porous surface at velocity of 2000 to 3000 feet per minute. Component ratios of the fibers in the nonwoven web were approximately 30% meltblown fibers and 70% spunbonded filaments. The forming surface was a flexible grid and comprised a sheet of ⅜ inch thick silicone foam rubber having an array of apertures therein. The apertures were 0.4 inch by 0.4 inch squares spaced 0.18 inches away from each other. The grid was adhered to a wire mesh support surface. The resulting nonwoven web had a basis weight of 1.3 osy. The resulting nonwoven web had projections that matched the cut-out 0.4 inch squares of the grid pattern and land areas that matched the land areas of the forming surface.

To determine the extent of concentration in the projections, the average basis weight of the fabric projections were determined by weighing these regions separately from the land areas. The projections exhibited a basis weight of 1.5 osy. Likewise, the basis weight of the land areas was determined. The land areas exhibited a basis weight of 1.0 osy. As can be seen, the difference in basis weight between the land areas and the projections for the fabric containing meltblown fibers is less than the difference obtained with only spunbond filaments. This is believed to be due to the presence of the meltblown fibers which diminish arrangement of the spunbond filaments during collection of the filaments on the forming surface.

Figure 11:
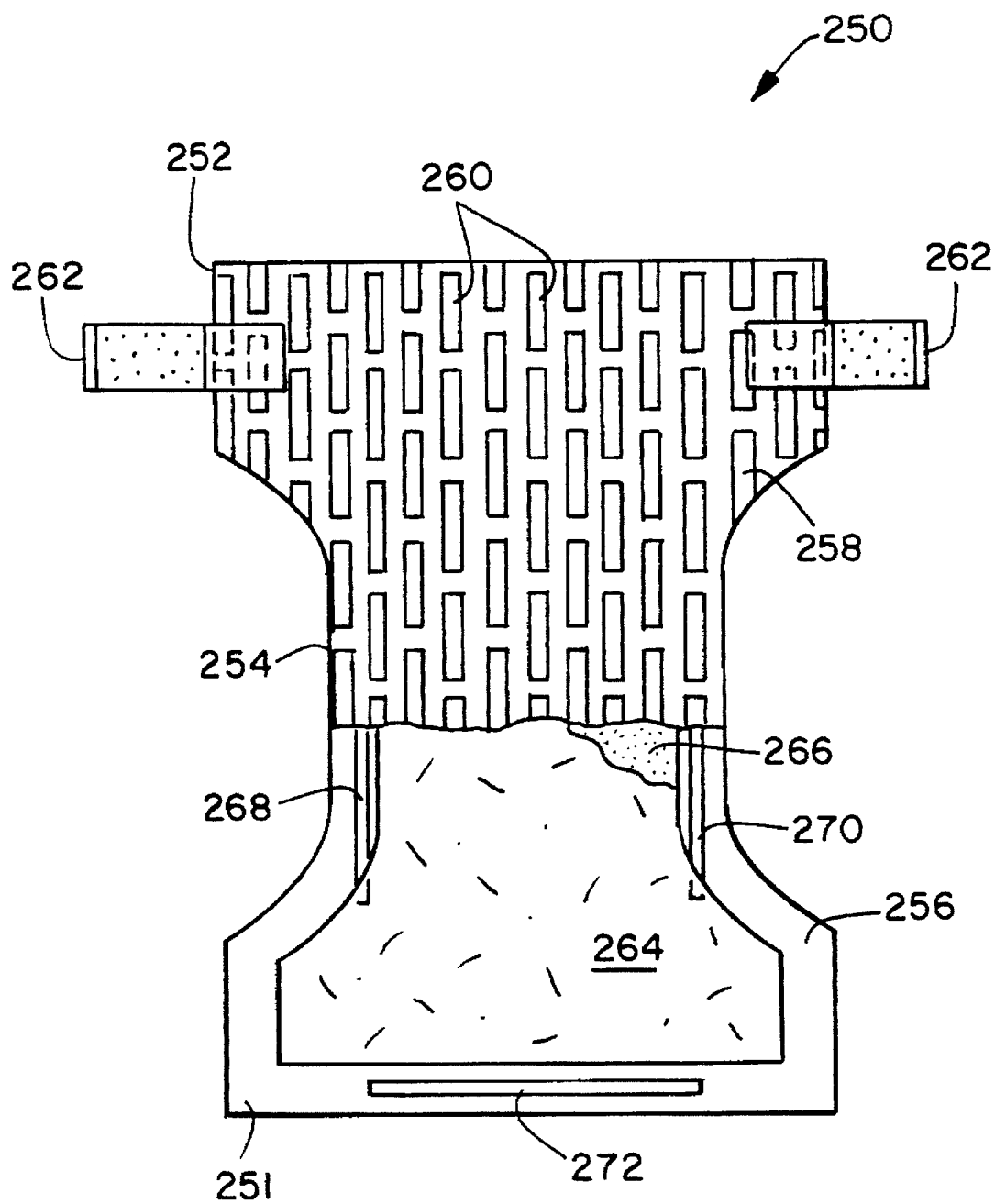
FIG. 11 is a diaper made according to an embodiment of the present invention.

As discussed above, the fabric of the present invention can be used to make a variety of useful products such as personal care products, garments, medical products, and cleaning products. The construction of such materials with nonwovens is well-known to those skilled in the art and each of those materials is not described in detail herein. However, as an example, a diaper 250 including a layer of fabric made according to the present invention is shown in FIG. 11 and described below.

The diaper 250 includes a front waistband panel section 251, a rear waistband panel section 252, and an intermediate section 254 which interconnects the front and rear waistband sections. The diaper comprises a substantially liquid impermeable outer cover layer 256, a liquid permeable liner layer 258, and an absorbent body 264 located between the outer cover layer and the liner layer. Fastening means, such as adhesive tapes 262 are employed to secure the diaper 250 on a wearer. The liner 258 and outer cover 256 are bonded to each other and to absorbent body 264 with lines and patterns of adhesive, such as a hot-melt, pressure-sensitive adhesive. Elastic members 268, 270 and 272 can be configured about the edges of the diaper for a close fit about the wearer.

The outer cover layer 256 is composed of a substantially liquid impermeable material such as a polymer film comprising polyethylene, polypropylene or the like. The outer cover layer 256 may alternatively be composed of a nonwoven fibrous web constructed to provide the desired level of liquid impermeability.

The liner layer 258 preferably comprises the shaped nonwoven fabric of the present invention. The liner layer 258 has a pattern of rectangular-shaped projections 260 which direct the flow of liquid across the liner layer and separate the absorbent from the wearer's skin. In the configuration shown in FIG. 11, the elongated projections 260 direct more liquid along the length of the projections than across the width of the liner layer 258. It is desirable that both the liner layer 258 and the absorbent body 264 be hydrophilic to absorb and retain aqueous fluids such as urine.

Although not shown in FIG. 11, the disposable diaper 250 may include additional fluid handling layers such as a surge layer, a transfer layer or a distribution layer. These layers may be separate layers or may be integral with the liner layer 256 or the absorbent pad 264.

While the invention has been described in detail with respect to specific embodiments thereof, it will be appreciated that those skilled in the art, upon obtaining an understanding of the foregoing, will readily conceive of alterations to, variations of and equivalents to these embodiments. Accordingly, the scope of the present invention should be assessed as that of the appending claims and any equivalents thereto.

We claim:

1. Nonwoven fabric having a length and a surface and comprising melt-spun and drawn continuous spunbond polymeric filaments extending substantially continuously along the length of the fabric, the filaments having an average diameter from about 6 to about 40 microns and forming an array of discrete surface features in the fabric, the spunbond filaments having a primary polymeric component extending continuously along the length of the filaments, the spunbond filaments being bonded together without the use of compression, and the fabric having an array of surface projections or apertures or a combination of surface projections and apertures determined by the array of discrete surface features on the foraminous surface upon which the drawn filaments were deposited prior to being bonded together under heating conditions and with an adhesive polymeric component which adheres the respective primary components of the spunbond filaments together, whereby the fabric is substantially uncompressed.

2. Nonwoven fabric as in claim 1 wherein the adhesive polymeric component includes melt-blown polymeric fibers.

3. Nonwoven fabric as in claim 1 wherein the surface features of the fabric each have a cross-sectional area extending between adjacent land areas, the cross-sectional area of at least some of the individual surface features of the fabric having a minimal dimension of at least 0.03 inches.

4. Nonwoven fabric as in claim 1 wherein the continuous spunbond filaments have a natural helical crimp.

5. Nonwoven fabric as in claim 1 wherein the continuous spunbond filaments have at least about 3.0 natural helical crimps per extended inch.

6. Nonwoven fabric as in claim 1 wherein the continuous polymeric spunbond filaments comprise multicomponent filaments, the multicomponent filaments comprising the primary polymeric component and the adhesive component and having a cross-section, a length, and a peripheral surface, the primary and adhesive components being arranged in substantially distinct zones across the cross-section of the multicomponent filaments and extending continuously along the length of the multicomponent filaments, the adhesive component constituting at least a portion of the peripheral surface of the multicomponent filaments continuously along the length of the multicomponent filaments.

7. Nonwoven fabric as in claim 1 wherein the surface features of the fabric include projections extending from the fabric, the projections being substantially uncompressed.

8. Nonwoven fabric as in claim 7 wherein the projections are substantially filled with the continuous filaments.

9. Nonwoven fabric as in claim 8 wherein the projections are separated by land areas, the projections having a basis weight and the land areas have a basis weight, the basis weight of the projections being greater than the basis weight of adjacent land areas.

10. Nonwoven fabric as in claim 9 wherein the land areas of the fabric have portions of higher density than other lower density portions, the higher density portions including filaments aligned with one another and forming bundles of filaments connecting adjacent projections.

11. Nonwoven fabric as in claim 7 wherein the projections have a height and a density gradient along the height of the projections.

12. Nonwoven fabric as in claim 9 wherein the basis weight of the projections is 30% greater than the basis weight of adjacent land areas.

13. Nonwoven fabric as in claim 9 wherein the fabric has a length and a width which define a reference surface area, the projections each having a cross-sectional area which forms part of the reference surface area and extends between adjacent land areas, the cross-sectional areas of the projections totaling from about 10 to about 95% of the reference surface area.

14. Nonwoven as in claim 13 wherein the cross-sectional areas of the projections total from about 25 to about 50% of the reference surface area.

15. Nonwoven as in claim 9 wherein the projections have a height of at least about 0.05 inches.

16. Nonwoven fabric as in claim 1 wherein the surface features of the fabric include apertures.

17. Nonwoven fabric as in claim 16 wherein the land areas have a basis weight, the basis weight of the land areas being substantially uniform.

18. A personal care absorbent article comprising a layer of the nonwoven fabric of claim 1.

19. An infant diaper comprising a layer of the nonwoven fabric of claim 1.

20. An adult incontinence product comprising a layer of the nonwoven fabric of claim 1.

21. A feminine care absorbent product comprising a layer of the nonwoven fabric of claim 1.

22. A training pant comprising a layer of the nonwoven fabric of claim 1.

23. A wound dressing comprising a layer of the nonwoven fabric of claim 1.

24. A garment comprising a layer of the nonwoven fabric of claim 1.

* * * * *

UNITED STATES PATENT AND TRADEMARK OFFICE
CERTIFICATE OF CORRECTION

PATENT NO. : 5,643,653
DATED : July 1, 1997
INVENTOR(S) : Griesbach, III et al

It is certified that error appears in the above-identified patent and that said Letters Patent is hereby corrected as shown below:

Column 1, line 41, "aperture" should read -- apertures -- ;

Column 3, line 18, "is to to" should read -- is to -- ;

Column 5, line 23, "a" should read -- at -- ;

Column 5, line 24, "discret" should read -- discrete -- ;

Column 5, line 34, "pressure:" should read -- pressure ; -- ;

Column 5, line 37, "foaming" should read -- forming -- ;

Column 6, line 51, "cross-sectional sectional" should read -- cross-sectional -- ;

Column 8, line 30, "microns    ," should read -- microns, -- ;

Column 16, line 54, "fried" should read -- filled -- ;

Column 17, line 11, "fabric--along," should read -- fabric-- -- ;

Column 17, line 43, "u," should read -- up -- ;

Column 20, line 36, "C-mine" should read -- diamine -- ;

UNITED STATES PATENT AND TRADEMARK OFFICE
CERTIFICATE OF CORRECTION

PATENT NO. : 5,643,653
DATED : July 1, 1997
INVENTOR(S) : Griesbach, III et al.

It is certified that error appears in the above-identified patent and that said Letters Patent is hereby corrected as shown below:

Column 5, line 17, "a)" should read -- a. -- ;

Column 5, line 20, "b)" should read -- b. -- ;

Column 5, line 21, "c)" should read -- c. -- ;

Column 6, line 1, "colection" should read -- collection -- ;

Column 7, line 25, "a" should read -- an -- ;

Column 7, line 29, "a" should read -- an -- ;

Column 7, line 34, "a" should read -- an -- ;

Signed and Sealed this

Ninth Day of December, 1997

Attest:

BRUCE LEHMAN

*Attesting Officer*     *Commissioner of Patents and Trademarks*